(12) United States Patent
Mercep et al.

(10) Patent No.: US 7,166,583 B2
(45) Date of Patent: Jan. 23, 2007

(54) 1,3-DIAZA-DIBENZOAZULENES AS INHIBITORS OF TUMOUR NECROSIS FACTOR PRODUCTION AND INTERMEDIATES FOR THE PREPARATION THEREOF

(75) Inventors: Mladen Mercep, Zagreb (HR); Milan Mesic, Zagreb (HR); Renata Rupcic, Zagreb (HR); Dijana Pesic, Sibenik (HR)

(73) Assignee: Pliva-Istrazivacki Institut d.o.o., Zagreb (HR)

( * ) Notice: Subject to any disclaimer, the term of this patent is extended or adjusted under 35 U.S.C. 154(b) by 0 days.

(21) Appl. No.: 10/515,711

(22) PCT Filed: May 20, 2003

(86) PCT No.: PCT/HR03/00025

§ 371 (c)(1),
(2), (4) Date: May 25, 2005

(87) PCT Pub. No.: WO03/099823

PCT Pub. Date: Dec. 4, 2003

(65) Prior Publication Data

US 2005/0227963 A1    Oct. 13, 2005

(30) Foreign Application Priority Data

May 23, 2002   (HR) .................. P 200020453 A

(51) Int. Cl.
*A61K 31/4162*    (2006.01)
*A61K 31/38*      (2006.01)
*A61K 31/335*     (2006.01)
*C07D 235/02*     (2006.01)
*C07D 337/14*     (2006.01)
*C07D 313/14*     (2006.01)

(52) U.S. Cl. .................. 514/63; 514/393; 514/431; 514/450; 548/110; 548/301.7; 549/4; 549/12; 549/214; 549/354

(58) Field of Classification Search .............. 514/63, 514/393, 431, 450; 548/110, 301.7; 549/4, 549/12, 214, 354
See application file for complete search history.

(56) References Cited

U.S. PATENT DOCUMENTS

| | | | |
|---|---|---|---|
| 3,711,489 A * | 1/1973 | Lombardino et al. | .... 546/273.1 |
| 3,781,294 A | 12/1973 | Lombardino | |
| 4,198,421 A | 4/1980 | Cherkofsky et al. | |
| 4,215,135 A | 7/1980 | Cherkofsky et al. | |
| 4,305,954 A | 12/1981 | Finizio | |

FOREIGN PATENT DOCUMENTS

| | | |
|---|---|---|
| EP | 0 372 445 | 6/1990 |
| FR | 2211218 | 7/1974 |
| HR | 20000310 | 2/2002 |
| WO | WO-91/18885 | 12/1991 |
| WO | WO-98/47892 | 10/1998 |
| WO | WO-01/87890 | 11/2001 |

OTHER PUBLICATIONS

Bresnihan, Treatment with Recombinant Human Interleukin-1 Receptor Antagonist (rhIL-1ra) in Rheumatoid Arthritis (RA); Results of a Randomized Double-Blind, Placebo-Controlled Multicenter trial, Arthrit. Rheum., 1996, 39:73.
Mori et al., Attenuation of Collagen-Induced Arthritis in 55-kDa TNF Receptor Type 1 (TNFR1)-IgG1-Treated and TNFR1-Deficient Mice, J. Immunol., 1996, 157:3178-3182.
Van Assche and Rutgeerts, Anti-TNF agents in Crohn's disease, Exp. Opin. Invest. Drugs, 2000, 9:103-111.
Keffer at al., Transgenic mice expressing human tumour necrosis factor: a predictive genetic model of arthritis, EMBO J., 1991, 10:4025-4031.
Elliott et al., Randmoised double-blind comparison of chimeric monoclonal antibody to tumor necrosis factor alpha (cA2) versus placebo in rheumatoid arthritis, The Lancet, 1994, 344:1105-1110.
Carswell et al., An endotoxin-induced serum factor that causes necrosis of tumors, Proc. Natl. Acad. Sci. U.S.A., 1975, 72:3666-3670.
Mattioli and Ghia, omega-Dialkylaminoalkyl Ethers of Phenyl-(5-substituted 1-phenyl-1H-pyrazol-4-yl)methanols with Analgesic and Anti-inflammatory Activity, J. Heterocyclic Chem., 1997, 34:963-968.
Dinarello, An Update on Human Interleukin-1: From Molecular Biology to Clinical Relevance, J. Clinical Immunology, 1985, 5:287.
Georgopoulos et al., Transmembrane TNF Is Sufficient To Induce Localized Tissue Toxicity and Chronic Inflammatory Arthritis In Transgenic Mice, J. Inflamm., 1996, 46:86-97.
Dinarello, Interleukin-1, Rev- Infect Disease, 1984, 6(1):51-95.
Pfeffer et al., Mice Deficient for the 55kd Tumor Necrosis Factor Receptor Are Resistant to Endotixic Shock, yet Succumb to L. monocytogenes Infection, Cell, 1993, 73:457-467.
Collier et al., The Abdominal Constriction Response and Its Suppression By Analgesis Drugs in the Mouse, Br. J. Pharmac. Chemother., 1968, 32:295-310.
Schweizer et al., Combined automated writhing/motility test for testing analgesics, Agents and Actions, 1988, 23:29-31.
Fukawa et al., A Method for Evaluating Analgesic Agents in Rats, J. Pharmacol. Meth., 1980, 4:251-259.
Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, J. Pharmac. Env. Therap., 1996, 279(3):1453-1461.
Lombardino, Synthesis of Some Novel Tetracyclic Imidazole Derivatives, J Heterocyclic Chem., 1974, 11:17-21.

* cited by examiner

*Primary Examiner*—Joseph K. McKane
*Assistant Examiner*—Joseph R. Kosack
(74) *Attorney, Agent, or Firm*—Darby & Darby

(57) ABSTRACT

The present invention relates to 1,3-diaza-dibenzoazulene derivatives, to their pharmacologically acceptable salts and solvates, to processes and intermediates for the preparation thereof as well as to their antiinflammatory effects, especially to the inhibition of tumor necrosis factor-α (TNF-α) production and the inhibition of interleukin-1 (IL-1) production as well as to their analgetic action.

13 Claims, No Drawings

1,3-DIAZA-DIBENZOAZULENES AS INHIBITORS OF TUMOUR NECROSIS FACTOR PRODUCTION AND INTERMEDIATES FOR THE PREPARATION THEREOF

This application is a National Stage under 35 U.S.C. §371 of PCT International Application No. PCT/HR03/00025, filed May 20, 2003, which claims the benefit under 35 U.S.C. §119(e) of prior Croatian Application No. P20020453A, filed May 23, 2002, the entire contents of which are incorporated herein by reference.

TECHNICAL FIELD

The present invention relates to 1,3-diaza-dibenzoazulene derivatives, to their pharmacologically acceptable salts and solvates, to processes and intermediates for the preparation thereof as well as to their antiinflammatory effects, especially to the inhibition of tumour necrosis factor-E (TNF-α) production and the inhibition of interleukin-1 (IL-1) production as well as to their analgetic action.

PRIOR ART

There are numerous literature data relating to various 1,3-diaza-dibenzoazulene derivatives and to the preparation thereof. It is well-known that 1,3-diaza-dibenzoazulene derivatives and salts thereof have an antiinflammatory action and represent a novel class of compounds having such an action. Thus in a series of patents (U.S. Pat. Nos. 3,711,489, 3,781,294 and CA 967,573) the preparation of dibenzoazulenes of imidazole class with various substituents such as trifluoromethyl, pyridyl, naphthyl, phenyl and substituted phenyl in 2-position is disclosed. Also the corresponding imidazoles with alkylthio substituents in 2-position possess a similar action (U.S. Pat. No. 4,198,421; EP 372,445 and WO 9,118,885).

There are also known 1-thia-dibenzoazulenes having aminoalkyloxy substituents on thiophene ring, which possess an antiinflammatory action (WO 01/878990).

According to our knowledge and to available literature data, dibenzoazulenes of imidazole class with hydroxyalkyl, alkyloxy, aminoalkyloxy, carboxy, acetyl or amino group on the imidazole ring, which represent an object of the present invention, have so far not been prepared or disclosed. It is not known either that such compounds could possess an antiinflammatory and/or analgetic action, which also represents an object of the present invention.

TNF-α is defined as a serum factor induced by endotoxin and causing tumour necrosis in vitro and in vivo (Carswell E A et al., *Proc. Natl. Acad. Sci. U.S.A.*, 1975, 72:3666–3670). Besides an antitumour action, TNF-α also possesses numerous other biological actions important in the homeostasis of organisms and in pathophysiological conditions. The main sources of TNF-α are monocytes-macrophages, T-lymphocytes and mastocytes.

The discovery that anti-TNF-α antibodies (cA2) have an action in treating patients with rheumatoid arthritis (RA) (Elliott M et al., *Lancet*, 1994, 344:1105–1110) led to an increased interest in finding novel TNF-α inhibitors as possible potent drugs for RA. Rheumatoid arthritis is an autoimmune chronic inflammatory disease characterized by irreversible pathological changes in the joints. In addition to RA theraphy, TNF-α antagonists may also be used in numerous pathological conditions and diseases such as spondylitis, osteoarthritis, gout and other arthritic conditions, sepsis, septic shock, toxic shock syndrom, atopic dermatitis, contact dermatitis, psoriasis, glomerulonephritis, lupus erythematosus, scleroderma, asthma, cachexia, chronic obstructive lung disease, congestive cardiac arrest, insulin resistance, lung fibrosis, multiple sclerosis, Crohn's disease, ulcerative colitis, viral infections and AIDS.

Some of the proofs indicating the biological importance of TNF-α were obtained by in vivo experiments in mice, in which mice genes for TNF-α or its receptor were inactivated. Such animals are resistant to collagen-induced arthritis (Mori L et al., *J. Immunol.*, 1996, 157:3178–3182) and to endotoxin-caused shock (Pfeffer K et al., *Cell*, 1993, 73:457–467). In animal assays where the TNF-α level was increased, a chronic inflammatory polyarthritis occurred (Georgopoulos S et al., *J. Inflamm.*, 1996, 46:86–97; Keffer J et al., *EMBO J.*, 1991, 10:4025–4031), which is similar to RA, and its pathological picture was alleviated by inhibitors of TNF-α production. The treatment of such inflammatory and pathological conditions usually includes the application of non-steroid antiinflammatory drugs and in more severe cases gold salts, D-penicillinamine or methotrexate are administered. Said drugs act symptomatically, but they do not stop the pathological process. Novel approaches in the therapy of rheumatoid arthritis are based upon drugs such as tenidap, leflunomide, cyclosporin, FK-506 and upon biomolecules neutralizing the TNF-α action. At present there are commercially available etanercept (Enbrel, Immunex/Wyeth), a fusion protein of the soluble TNF-α receptor, and infliximab (Remicade, Centocor), a chimeric monoclonal human and mouse antibody. Besides in RA therapy, etanercept and infliximab are also registered for the therapy of Crohn's disease (*Exp. Opin. Invest. Drugs,* 2000, 9:103).

In an optimum RA therapy, besides inhibition of TNF-α secretion, also the inhibition of IL-1 secretion is very important since IL-1 is an important cytokin in cell regulation and immunoregulation as well as in pathophysiological conditions such as inflammation (Dinarello C A et al., *Rev. Infect. Disease,* 1984, 6:51). Well-known biological activities of IL-1 are: activation of T-cells, induction of elevated temperature, stimulation of secretion of prostaglandine or collagenase, chemotaxia of neutrophils and reduction of iron level in plasma (Dinarello C A, *J. Clinical Immunology,* 1985, 5:287). Two receptors to which IL-1 may bind are well-known: IL-1RI and IL-1RII. IL-1RI transfers a signal intracellularly, whereas IL-1RII, though situated on the cell surface, does not transfer a signal inside the cell. Since IL1-RII binds IL-1 as well as IL1-RI, it may act as a negative regulator of IL-1 action. Besides this mechanism of signal transfer regulation, another natural antagonist of IL-1 receptor, IL-1ra, is present in cells. This protein binds to IL-1RI, but does not bring about a stimulation thereof. The potency of IL-1ra in stopping the transfer of the signal stimulated by IL-1 is not high and its concentration has to be 500 times higher than that of IL-1 in order to achieve a break in the signal transfer. Recombinant human IL-1ra (Amgen) was clinically tested (Bresnihan B et al., *Arthrit. Rheum.,* 1996, 39:73) and the obtained results indicated an improvement of the clinical picture in RA patients over an placebo. These results indicate the importance of the inhibition of IL-1 action in treating diseases such as RA where IL-1 production is disturbed. Since there exists a synergistic action of TNF-α and IL-1, dual TNF-α and IL-1 inhibitors may be used in treating conditions and diseases related to an enhanced secretion of TNF-α and IL-1.

Inventive Solution

The present invention relates to the compounds of 1,3-diaza-dibenzoazulene of the formula I:

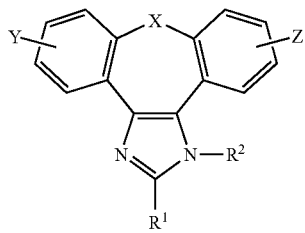

I wherein

X may be $CH_2$ or a hetero atom such as O, S, S(=O), S(=O)$_2$, or $NR^a$, wherein $R^a$ is hydrogen or a protecting group, said protecting group being selected from the group consisting of alkyl, alkanoyl, alkoxycarbonyl, arylmethoxycarbonyl, aroyl, arylalkyl, alkylsilyl or alkylsilylalkoxyalkyl;

Y and Z independently from each other denote one or more identical or different substituents linked to any available carbon atom, and may be hydrogen, halogen, $C_1$–$C_4$ alkyl, $C_2$–$C_4$ alkenyl, $C_2$–$C_4$ alkinyl, halo-$C_1$–$C_4$ alkyl, hydroxy, $C_1$–$C_4$ alkoxy, trifluoromethoxy, $C_1$–$C_4$ alkanoyl, amino, amino-$C_1$–$C_4$-alkyl, N-($C_1$–$C_4$-alkyl)amino, N,N-di($C_1$–$C_4$ alkyl)amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano, nitro;

$R^1$ may be CHO, $CH_3OCOH{=}CH$, $(CH_2)_mOH$, wherein m is as defined below, or a substituent of the formula II:

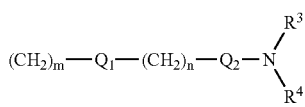

II wherein $R^3$ and $R^4$ simultaneously or independently from each other may be hydrogen, $C_1$–$C_4$-alkyl, aryl or together with N have the meaning of an optionally substituted heterocycle or heteroaryl;

m represents an integer from 1 to 3;

n represent an integer from 0 to 3;

$Q_1$ and $Q_2$ represent, independently from each other, oxygen, sulfur or groups:

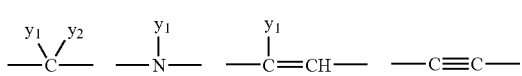

wherein the substituents $y_1$ and $y_2$ independently from each other may be hydrogen, halogen, an optionally substituted $C_1$–$C_4$ alkyl or aryl, hydroxy, $C_1$–$C_4$ alkoxy, $C_1$–$C_4$ alkanoyl, thiol, $C_1$–$C_4$ alkylthio, sulfonyl, $C_1$–$C_4$ alkylsulfonyl, sulfinyl, $C_1$–$C_4$ alkylsulfinyl, cyano, nitro or together form carbonyl or imino group;

$R^2$ has the meaning of hydrogen, optionally substituted $C_1$–$C_7$ alkyl or aryl or a protecting group: formyl, $C_1$–$C_7$ alkanoyl, $C_1$–$C_7$ alkoxycarbonyl, arylalkyloxycarbonyl, aroyl, arylalkyl, $C_1$–$C_7$ alkylsilyl, $C_6H_5CH_2CH_2$ or $(CH_3)_3SiCH_2CH_2OCH_2$;

as well as to pharmacologically acceptable salts and solvates thereof.

The term "halo", "hal" or "halogen" relates to a halogen atom which may be fluorine, chlorine, bromine or iodine.

The term "alkyl" relates to alkyl groups with the meaning of alkanes wherefrom radicals are derived, which radicals may be straight, branched or cyclic or a combination of straight and cyclic ones and branched and cyclic ones. The preferred straight or branched alkyls are e.g. methyl, ethyl, propyl, iso-propyl, butyl, sec-butyl and tert-butyl. The preferred cyclic alkyls are e.g. cyclopentyl or cyclohexyl.

The term "haloalkyl" relates to alkyl groups which must be substituted with at least one halogen atom. The most frequent haloalkyls are e.g. chloromethyl, dichloromethyl, trifluoromethyl or 1,2-dichloropropyl.

The term "alkenyl" relates to alkenyl groups having the meaning of hydrocarbon radicals, which may be straight, branched or cyclic or are a combination of straight and cyclic ones or branched and cyclic ones, but having at least one carbon-carbon double bond. The most frequent alkenyls are ethenyl, propenyl, butenyl or cyclohexenyl.

The term "alkinyl" relates to alkinyl groups having the meaning of hydrocarbon radicals, which are straight or branched and contain at least one and at most two carbon-carbon triple bonds. The most frequent alkinyls are e.g. ethinyl, propinyl or butinyl.

The term "alkoxy" relates to straight or branched chains of alkoxy group. Examples of such groups are methoxy, propoxy, prop-2-oxy, butoxy, but-2-oxy or methylprop-2-oxy.

The term "aryl" relates to groups having the meaning of an aromatic ring, e.g. phenyl, as well as to fused aromatic rings. Aryl contains one ring with at least 6 carbon atoms or two rings with totally 10 carbon atoms and with alternating double (resonant) bonds between carbon atoms. The most freqently used aryls are e.g. phenyl or naphthyl. In general, aryl groups may be linked to the rest of the molecule by any available carbon atom via a direct bond or via a $C_1$–$C_4$ alkylene group such as methylene or ethylene.

The term "heteroaryl" relates to groups having the meaning of aromatic and partially aromatic groups of a monocyclic or bicyclic ring with 4 to 12 atoms, at least one of them being a hetero atom such as O, S or N, and the available nitrogen atom or carbon atom is the binding site of the group to the rest of the molecule either via a direct bond or via a $C_1$–$C_4$ alkylene group defined earlier. Examples of this type are thiophenyl, pyrrolyl, imidazolyl, pyridinyl, oxazolyl, thiazolyl, pyrazolyl, tetrazolyl, pirimidinyl, pyrazinyl, quinolinyl or triazinyl.

The term "heterocycle" relates to five-member or six-member, completely saturated or partly unsaturated heterocyclic groups containing at least one hetero atom such as O, S or N, and the available nitrogen atom or carbon atom is the binding site of the group to the rest of the molecule either via a direct bond or via a $C_1$–$C_4$ alkylene group defined earlier. The most frequent examples are morpholinyl, piperidinyl, piperazinyl, pyrrolidinyl, pirazinyl or imidazolyl.

The term "alkanoyl" group relates to straight chains of acyl group such as formyl, acetyl or propanoyl.

The term "aroyl" group relates to aromatic acyl groups such as benzoyl.

The term "optionally substituted alkyl" relates to alkyl groups which may be optionally additionally substituted with one, two, three or more substituents. Such substituents may be halogen atom (preferably fluorine or chlorine), hydroxy, $C_1$–$C_4$ alkoxy (preferably methoxy or ethoxy), thiol, $C_1$–$C_4$ alkylthio (preferably methylthio or ethylthio), amino, N-($C_1$–$C_4$) alkylamino (preferably N-methylamino or N-ethylamino), N,N-di($C_1$–$C_4$-alkyl)-amino (preferably dimethylamino or diethylamino), sulfonyl, $C_1$–$C_4$ alkylsulfonyl (preferably methylsulfonyl or ethylsulfonyl), sulfinyl, $C_1$–$C_4$ alkylsulfinyl (preferably methylsulfinyl).

The term "optionally substituted alkenyl" relates to alkenyl groups optionally additionally substituted with one, two or three halogen atoms. Such substituents may be e.g. 2-chloroethenyl, 1,2-dichloroethenyl or 2-bromo-propene-1-yl.

The term "optionally substituted aryl, heteroaryl or heterocycle" relates to aryl, heteroaryl or heterocyclic groups which may be optionally additionally substituted with one or two substituents. The substituents may be halogen (preferably chlorine or fluorine), $C_1$–$C_4$ alkyl (preferably methyl, ethyl or isopropyl), cyano, nitro, hydroxy, $C_1$–$C_4$ alkoxy (preferably methoxy or ethoxy), thiol, $C_1$–$C_4$ alkylthio (preferably methylthio or ethylthio), amino, N-($C_1$–$C_4$) alkylamino (preferably N-methylamino or N-ethylamino), N,N-di($C_1$–$C_4$-alkyl)-amino (preferably N,N-dimethylamino or N,N-diethylamino), sulfonyl, $C_1$–$C_4$ alkylsulfonyl (preferably methylsulfonyl or ethylsulfonyl), sulfinyl, $C_1$–$C_4$ alkylsulfinyl (preferably methylsulfinyl).

When X has the meaning of $NR^a$ and $R^a$ has the meaning of a protecting group, then $R^a$ relates to groups such as alkyl (preferably methyl or ethyl), alkanoyl (preferably acetyl), alkoxycarbonyl (preferably methoxycarbonyl or tert-butoxycarbonyl), arylmethoxycarbonyl (preferably benzyloxycarbonyl), aroyl (preferably benzoyl), arylalkyl (preferably benzyl), alkylsilyl (preferably trimethylsilyl) or alkylsilylalkoxyalkyl (preferably trimethylsilylethoxymethyl).

When $R^3$ and $R^4$ together with N have the meaning of heteroaryl or heterocycle, this means that such heteroaryls or heterocycles have at least one carbon atom replaced by a nitrogen atom through which the groups are linked to the rest of the molecule. Examples of such groups are morpholine-4-yl, piperidine-1-yl, pyrrolidine-1-yl, imidazole-1-yl or piperazine-1-yl.

The term "pharmaceutically suitable salts" relates to salts of the compounds of the formula I and includes e.g. salts with $C_1$–$C_4$ alkylhalides (preferably methyl bromide, methyl chloride) (quaternary ammonium salts), with inorganic acids (hydrochloric, hydrobromic, phosphoric, metaphosphoric, nitric or sulfuric acids) or with organic acids (tartaric, acetic, citric, maleic, lactic, fumaric, benzoic, succinic, methane sulfonic or p-toluene sulfonic acids).

Some compounds of the formula I may form salts with organic or inorganic acids or bases and these are also included in the present invention.

Solvates (most frequently hydrates) which may be formed by compounds of the formula I or salts thereof are also an object of the present invention.

Depending upon the nature of particular substituents, the compounds of the formula I may have geometric isomers and one or more chiral centres so that there can exist enantiomers or diastereoisomers. The present invention also relates to such isomers and mixtures thereof, including racemates.

The present invention also relates to all possible tautomeric forms of particular compounds of the formula I.

A further object of the present invention is the preparation of compounds of the formula I according to processes comprising a) for the compounds of the formula I, wherein $R^1$ has the meaning of CHO, a formylation of the compounds of the formula III

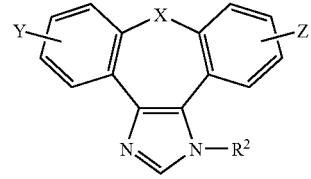

b) for the compounds of the formula I, wherein $Q_1$ has the meaning of —O—, a reaction of the alcohols of the formula IV

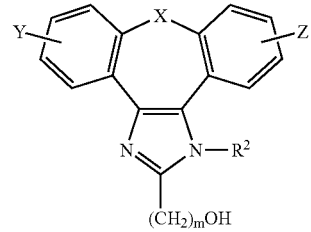

with compounds of the formula V

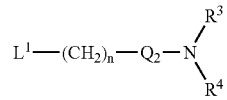

wherein $L^1$ has the meaning of the leaving group;

c) for the compounds of the formula I, wherein $Q_1$ has the meaning of —O—, —NH—, —S— or —C≡C—, a reaction of the compounds of the formula IVa

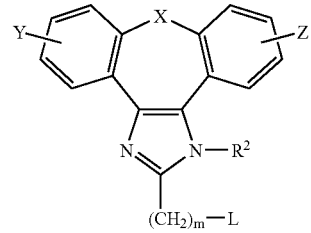

wherein L has the meaning of a leaving group, with compounds of the formula Va

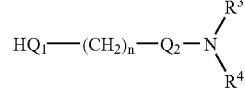

d) for the compounds, wherein $Q_1$ has the meaning of —O—, —NH— or —S—, a reaction of compounds of the formula IVb

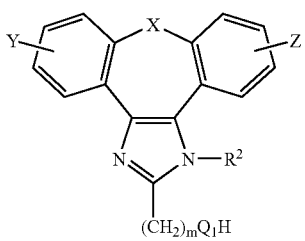

IVb with compounds of the formula V, wherein $L^1$ has the meaning of a leaving group;

e) for the compounds of the formula I, wherein $Q_1$ has the meaning of —C≡C—, a reaction of the compounds of the formula IVb, wherein $Q_1$ has the meaning of carbonyl, with phosphorous ylides.

Preparation Methods:

a) The compounds of the formula I, wherein $R^1$ has a meaning of CHO may be obtained by formylation of the compounds of the formula III, wherein $R^2$ has a meaning of protecting group by the action of n-butyl-lithium at decreased temperature (preferably −80° C.) within 0.5 hours, followed by the addition of N,N-dimethylformamide and carrying out the reaction at room temperature. The products may be isolated and purified by crystallization or chromatography on a silica gel column.

The starting substances for the preparation of the compounds of the formula III, corresponding dibenzo-azulenes of the formula IIIa:

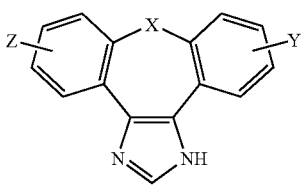

IIIa are already known or are prepared by methods disclosed for the preparation of analogous compounds.

Thus, e.g. compounds of the formula III may be prepared starting from α-diketone dibenzo-oxepine or dibenzo-thiepine. By the action of aldehyde and ammonium acetate to α-diketone, the cyclization and formation of condensed imidazole ring occur. By the reaction of paraformaldehyde a nonsubstituted imidazole ring is formed. A similar reaction course is already disclosed in literature (Lombardino J G et al., *J. Heterocyclic Chem.*, 1974, 11: 17–21). By the protection of free NH-group (WO 98/47892) of compounds of the formula IIIa by the action of compounds of the formula IIIb:

$R^2$—$L^2$   IIIb wherein $L^2$ has the meaning of leaving group such as halogen (most frequently chlorine or bromine), the compounds III as a mixture of 1- and 3-substituted isomers are formed. The reaction is carried out in organic solvents such as dimethylsulfoxide, tetrahydrofuran, benzene or toluene under the addition of a strong base such as sodium hydride at an increased temperature from 50° C. to 150° C. during 1 to 5 hours. The crude product may be isolated and purified by recrystallization or chromatography on a silica gel column.

b) Compounds of the formula I according to the present process may be prepared by reaction of alcohols of the formula IV and compounds of the formula V, wherein $L^1$ has the meaning of a leaving group that may be a halogen atom (most frequently bromine, iodine or chlorine) or a sulfonyloxy group (most frequently trifluoromethylsulfonyloxy or p-toluenesulfonyloxy). The condensation reaction may be carried out according to methods disclosed for the preparation of analogous compounds (Menozzi G et al., *J. Heterocyclic Chem.*, 1997, 34:963–968 or WO 01/87890). The reaction is carried out at a temperature from 20° C. to 100° C. during 1 to 24 hours in a two-phase system (preferably with 50% NaOH/toluene) in the presence of a phase transfer catalyst (preferably benzyl triethyl ammonium chloride, benzyl triethyl ammonium bromide, cetyl trimethyl bromide). After the treatment of the reaction mixture, the products formed are isolated by recrystallization or chromatography on a silica gel column.

The starting substances, alcohols of the formula IV, may be prepared from the compounds of the formula I, wherein $R^1$ has the meaning of a suitable functional group. Thus, e.g. alcohols of the formula IV may be obtained by the reduction of an aldehyde, carboxyl or alkyloxycarbonyl group (e.g. methyloxycarbonyl or ethyloxycarbonyl) by using metal hydrides such as lithium aluminum hydride or sodium borohydride. Further, alcohols of the formula IV may be prepared by the hydrolysis of the corresponding esters in an alkaline or acidic medium.

The starting compounds of the formula V are already known or are prepared according to methods disclosed for the preparation of analogous compounds.

c) Compounds of the formula I according to the present process may be prepared by reacting compounds of the formula IVa, wherein L has the meaning of a leaving group defined earlier for $L^1$, and compounds of the formula Va, wherein $Q_1$ has the meaning of oxygen, nitrogen, sulfur or —C≡C—. The most suitable condensation reactions are reactions of nucleophilic substitution on a saturated carbon atom as disclosed in the literature.

The starting compounds of the formula IVa (most frequently halides) may be obtained by halogenation (e.g. bromination or chlorination) of compounds of the formula IV with usual halogenating agents (hydrobromic acid, $PBr_3$, $SOCl_2$ or $PCl_5$) by processes as disclosed in the literature. The obtained compounds may be isolated or may be used without isolation as suitable intermediates for the preparation of the compounds of the formula I.

The starting compounds of the formula Va are already known or are prepared according to methods disclosed for the preparation of analogous compounds.

d) The compounds of the formula I, wherein $Q_1$ has the meaning of —O—, —NH— or —S—, may be prepared by condensation of the compounds of the formula IVb and of compounds of the formula V, wherein $L^1$ has the meaning of a leaving group defined earlier. The reaction may be carried out at reaction conditions disclosed in method b) or under conditions of reactions of nucleophilic substitution disclosed in the literature.

The starting alcohols, amines and thiols may be obtained by a reaction of water, ammonia or hydrogen sulfide with compounds IVa according to processes disclosed in the literature.

e) The alcohols of the structure IV may be oxidized to corresponding compounds of the formula IVb, wherein $Q_1$ has the meaning of carbonyl and which may further, by reaction with corresponding ylide reagents, result in a prolongation of the chain and in the formation of an alkenyl substituent with carbonyl or ester groups as disclosed in HR patent application No. 20000310.

Besides the above-mentioned reactions, the compounds of the formula I may be prepared by transforming other compounds of the formula I and it is to be understood that the present invention also comprises such compounds and processes. A special example of a change of a functional group is the reaction of the aldehyde group with chosen phosphorous ylides resulting in a prolongation of the chain and the formation of an alkenyl substituent with carbonyl or ester groups as disclosed in HR patent application No. 20000310. These reactions are carried out in solvents such as benzene, toluene or hexane at elevated temperature (most frequently at boiling temperature).

By reacting the compounds of the formula IVa with 1-alkyne in an alkaline medium (such as sodium amide in ammonia) the compounds of the formula I, wherein $Q_1$ is —C≡C—, are obtained. The reaction conditions of this process are disclosed in the literature. At similar reaction conditions (nucleophilic substitution) various ether, thioether or amine derivatives may be prepared.

The formylation of the compounds of the formula I by processes such as e.g. Vilsmeier acylation or reaction of n-BuLi and N,N-dimethylformamide is a further general example of a transformation. The reaction conditions of these processes are well-known in the literature.

By hydrolysis of the compounds of the formula I having nitrile, amide or ester groups, there may be prepared compounds with a carboxyl group, which are suitable intermediates for the preparation of other compounds with novel functional groups such as e.g. esters, amides, halides, anhydrides, alcohols or amines.

Oxidation or reduction reactions are a further possibility of the change of substituents in the compounds of the formula I. Most frequently used oxidation agents are peroxides (hydrogen peroxide, m-chloroperbenzoic acid or benzoyl peroxide) or permanganate, chromate or perchlorate ions. Thus e.g. by the oxidation of an alcohol group by pyridinyl dichromate or pyridinyl chlorochromate, an aldehyde group is formed, which may be converted to a carboxyl group by further oxidation. By oxidation of the compounds of the formula I, wherein $R^1$ has the meaning of alkyl, with lead tetraacetate in acetic acid or with N-bromosuccinimide using a catalytic amount of benzoyl peroxide, a corresponding carbonyl derivative is obtained.

By a selective oxidation of alkylthio group, alkylsulfinyl or alkylsulfonyl groups may be prepared.

By the reduction of the compounds with a nitro group, the preparation of amino compounds is made possible. The reaction is carried out under usual conditions of catalytic hydrogenation or electrochemically. By catalytic hydrogenation using palladium on carbon, alkenyl substituents may be converted to alkyl ones or nitrile group can be converted to aminoalkyl.

Various substituents of the aromatic structure in the compounds of the formula I may be introduced by standard substitution reactions or by usual changes of individual functional groups. Examples of such reactions are aromatic substitutions, alkylations, halogenation, hydroxylation as well as oxidation or reduction of substituents. Reagents and reaction conditions are known from the literature. Thus e.g. by aromatic substitution a nitro group is introduced in the presence of concentrated nitric acid and sulfuric acid. By using acyl halides or alkyl halides, the introduction of an acyl group or an alkyl group is made possible. The reaction is carried out in the presence of Lewis acids such as aluminum- or iron-trichloride in conditions of Friedel-Craft reaction. By the reduction of the nitro group, an amino group is obtained, which is by diazotizing reaction converted to a suitable starting group, which may be replaced with one of the following groups: H, CN, OH, Hal.

In order to prevent undesired interaction in chemical reactions, it is often necessary to protect certain groups such as e.g. hydroxy, amino, thio or carboxy. For this purpose a great number of protecting groups may be used (Green T W, Wuts P G H, Protective Groups in Organic Synthesis, John Wiley and Sons, 1999) and the choice, use and elimination thereof are conventional methods in chemical synthesis.

A convenient protection for amino or alkylamino groups are groups such as e.g. alkanoyl (acetyl), alkoxycarbonyl (methoxycarbonyl, ethoxycarbonyl or tert-butoxycarbonyl); arylmethoxycarbonyl (benzyloxycarbonyl), aroyl (benzoyl) or alkylsilyl (trimethylsilyl or trimethylsilylethoxymethyl) groups. The conditions of removing a protecting group depend upon the choice and the characteristics of this group. Thus e.g. acyl groups such as alkanoyl, alkoxycarbonyl or aroyl may be eliminated by hydrolysis in the presence of a base (sodium hydroxide or potassium hydroxide), tert-butoxycarbonyl or alkylsilyl (trimethylsilyl) may be eliminated by treatment with a suitable acid (hydrochloric, sulfuric, phosphoric or trifluoroacetic acid), whereas arylmethoxycarbonyl group (benzyloxycarbonyl) may be eliminated by hydrogenation using a catalyst such as palladium on carbon.

Salts of the compounds of the formula I may be prepared by generally known processes such as e.g. by reacting the compounds of the formula I with a corresponding base or acid in an appropriate solvent or solvent mixture e.g. ethers (diethylether) or alcohols (ethanol, propanol or isopropanol).

Another object of the present invention concerns the use of the present compounds in the therapy of inflammatory diseases and conditions, especially all diseases and conditions induced by excessive TNF-α and IL-1 secretion.

An effective dose of inhibitors of production of cytokins or inflammation mediators, which are the object of the present invention, or pharmacologically acceptable salts thereof may be used in the production of drugs for the treatment and prophylaxis of any pathological condition or disease induced by excessive unregulated production of cytokines or inflammation mediators.

The present invention more specifically relates to an effective dose of TNF-α inhibitor, which may be determined by usual methods.

Further, the present invention relates to a pharmaceutical formulation containing an effective non-toxic dose of the present compounds as well as pharmaceutically acceptable carriers or solvents.

The preparation of pharmaceutical formulations may include blending, granulating, tabletting and dissolving the ingredients. Chemical carriers may be solid or liquid. Solid carriers may be lactose, sucrose, talcum, gelatine, agar, pectin, magnesium stearate, fatty acids etc. Liquid carriers may be syrups, oils such as olive oil, sunflower oil or soya bean oil, water etc. Similarly, the carrier may also contain a component for a sustained release of the active component such as e.g. glyceryl monostearate or glyceryl distearate. Various forms of pharmaceutical formulations may be used. By the use of a solid carrier there may be prepared tablets, hard gelatine capsules, powder or granules that may be administered in capsules per os. The amount of the solid carrier may vary, but it is mainly from 25 mg to 1 g. If a liquid carrier is used, the formulation would be in the form of a syrup, emulsion, soft gelatine capsules, sterile injectable liquids such as ampoules or non-aqueous liquid suspensions.

Compounds according to the present invention may be applied per os, parenterally, locally, intranasally, intrarectally and intravaginally. The parenteral route herein means intravenous, intramuscular and subcutaneous applications. Appropriate formulations of the present compounds may be used in the prophylaxis as well as in the treatment of inflammatory diseases induced by an excessive unregulated production of cytokins or inflammation mediators, primarily TNF-α. They comprise e. g. rheumatoid arthritis, rheumatoid spondylitis, osteoarthritis and other arthritic pathological conditions and diseases, eczemas, psoriasis and other inflammatory skin conditions, inflammatory eye diseases, Crohn's disease, ulcerative colitis and asthma.

The inhibitory action of the present compounds upon TNF-α and IL-1 secretion was determined by the following in vitro and in vivo experiments:

Determination of TNF-α and IL-1 Secretion in Human Peripheral Blood Mononuclear Cells in Vitro Human peripheral blood mononuclear cells (PBMC) were prepared from heparinized whole blood after separating PBMC on Ficoll-Paque™Plus (Amersham-Pharmacia). To determine the TNF-α level, $3.5-5 \times 10^4$ cells were cultivated in a total volume of 200 µl for 18 to 24 hours on microtitre plates with a flat bottom (96 wells, Falcon) in RPMI 1640 medium, into which there were added 10% of FBS (Fetal Bovine Serum, Biowhittaker) previously inactivated at 56° C./30 min, 100 units/ml of penicillin, 100 mg/ml of streptomycin and 20 mM HEPES (GIBCO). The cells were incubated at 37° C. in an atmosphere with 5% $CO_2$ and 90% humidity. In a negative control the cells were cultivated only in the medium (NC), whereas in a positive control TNF-α secretion was triggered by adding 1 ng/ml of lipopolysaccharides (LPS, *E. coli* serotype 0111:B4, SIGMA) (PC). The effect of the tested substances upon TNF-α secretion was investigated after adding them into cultures of cells stimulated by LPS (TS). The TNF-α level in the cell supernatant was determined by ELISA procedure according to the suggestions of the producer (R&D Systems). The test sensitivity was <3 pg/ml TNF-α. The IL-1 level was determined in an assay under the same conditions and with the same number of cells and the same concentration of the stimulus by ELISA procedure (R&D Systems). The percentage of inhibition of TNF-α or IL-1 production was calculated by the equation:

% inhibition=$[1-(TS-NC)/(PC-NC)]*100$.

The $IC_{50}$ value was defined as the substance concentration, at which 50% of TNF-α production were inhibited.

Compounds showing $IC_{50}$ with 20 µM or lower concentrations are active.

Determination of TNF-α and IL-1 Secretion in Mouse Peritoneal Macrophages in Vitro In order to obtain peritoneal macrophages, Balb/C mouse strain males, age 8 to 12 weeks, were injected i.p. with 300 µg of zymosan (SIGMA) dissolved in a phosphate buffer (PBS) in a total volume of 0.1 ml/mouse. After 24 hours the mice were euthanized according to the Laboratory Animal Welfare Act. The peritoneal cavity was washed with a sterile physiological solution (5 ml). The obtained peritoneal macrophages were washed twice with a sterile physiological solution and, after the last centrifugation (350 g/10 min), resuspended in RPMI 1640, into which 10% of FBS portion were added. In order to determine TNF-α secretion, $5 \times 10^4$ cells/well were cultivated in a total volume of 200 µl for 18 to 24 hours on microtitre plates with a flat bottom (96 wells, Falcon) in RPMI 1640 medium, into which 10% of fetal bovine serum (FBS, Biowhittaker) inactivated by heat, 100 units/ml of penicillin, 100 mg/ml of streptomycin, 20 mM HEPES and 50 µM 2-mercaptoethanol (all of GIBCO) were added. The cells were incubated at 37° C. in an atmosphere with 5% $CO_2$ and 90% humidity. In a negative control the cells were cultivated only in a medium (NC), whereas in a positive control the TNF-α secretion was triggered by adding 10 ng/ml of lipopolysaccharides (LPS, *E. coli* serotype 0111:B4, SIGMA) (PC). The effect of the substances upon the TNF-α secretion was investigated after adding them into cultures of cells stimulated with LPS (TS). The TNF-α and IL-1 levels in the cell supernatant were determined by ELISA procedure specific for TNF-α and IL-1 (R&D Systems, Biosource). The IL-1 level was determined in an assay identical to the assay for TNF-α by ELISA procedure (R&D Systems). The percentage of inhibition of TNF-α or IL-I production was calculated by the equation:

% inhibition=$[1-(TS-NC)/(PC-NC)]*100$.

The $IC_{50}$ value was defined as the substance concentration, at which 50% of TNF-α production were inhibited.

Compounds showing $IC_{50}$ with 10 µM or lower concentrations are active.

In Vivo Model of LPS-Induced Excessive TNF-α or IL-1 Secretion in Mice

TNF-α or IL-1 secretion in mice was induced according to the already disclosed method (Badger A M et al., *J. Pharmac. Env. Therap.*, 1996, 279:1453–1461). Balb/C males, age 8 to 12 weeks, in groups of 6 to 10 animals were used. The animals were treated p.o. either with a solvent only (in negative and in positive controls) or with solutions of substances 30 minutes prior to i.p. treatment with LPS (*E. coli* serotype 0111:B4, Sigma) in a dosis of 1–25 µg/animal. Two hours later the animals were euthanized by means of i.p. Roumpun (Bayer) and Ketanest (Parke-Davis) injection. A blood sample of each animal was taken into a Vacutainer tube (Becton Dickinson) and the plasma was separated according to the producer's instructions. The TNF-α level in the plasma was determined by ELISA procedure (Biosource, R&D Systems) according to the producer's instructions. The test sensitivity was <3 pg/ml TNF-α. The IL-1 level was determined by ELISA procedure (R&D Systems). The percentage of inhibition of TNF-α or IL-1 production was calculated by the equation:

% inhibition=$[1-(TS-NC)/(PC-NC)]*100$.

Active are the compounds showing 30% or more inhibition of TNF-α production at a dosis of 10 mg/kg.

Writhing Assay for Analgetic Activity

In this assay pain is induced by the injection of an irritant, most frequently acetic acid, into the peritoneal cavity of mice. Animals react with characteristic writhings, which has given the name of the assay (Collier H O J et al., *Pharmac. Chemother.*, 1968, 32:295–310; Fukawa K et al., *J. Pharmacol. Meth.*, 1980, 4:251–259; Schweizer A et al., *Agents Actions*, 1988, 23:29–31). The assay is convenient for the determination of analgetic activity of compounds. Procedure: male Balb/C mice (Charles River, Italy), age 8 to 12 weeks, were used. A control group received methyl cellulose p.o. 30 minutes prior to i.p. application of acetic acid in a concentration of 0.6%, whereas test groups received standard (acetylsalicylic acid) or test substances in methyl cellulose p.o. 30 minutes prior to i.p. application of 0.6% acetic acid (volume 0.1 ml/10 g). The mice were placed individually under glass funnels and the number of writhings was registered for 20 minutes for each animal. The percentage of writhing inhibition was calculated according to the equation:

% inhibition=(mean value of number of writhings in the control group−number of writhings in the test group)/number of writhings in the control group* 100.

Active are the compounds showing such analgetic activity as acetylsalicylic acid or better.

In Vivo Model of LPS-induced Shock in Mice

Male Balb/C mice (Charles River, Italy), age 8 to 12 weeks, were used. LPS isolated from *Serratie marcessans* (Sigma, L-6136) was diluted in sterile physiological solution. The first LPS injection was administered intradermally in a dose of 4 μg/mouse. 18 to 24 hours later, LPS was administered i.v. in a dose of 200 μg/mouse. A control group received two LPS injections as disclosed above. The test groups received substances p.o. half an hour prior to each LPS application. Survival after 24 hours was observed.

Active are the substances at which the survival at a dosis of 30 mg/kg was 40% or more.

Compounds from Examples 8 and 9 show activity in at least two investigated assays though these results only represent an illustration of biological activity of compounds and should not limit the invention in any way.

PREPARATION PROCESSES WITH EXAMPLES

The present invention is illustrated by the following Examples which are in no way a limitation thereof.

Example 1

1-Methyl-1H-8-oxa-1,3-diaza-dibenzo[e,h]azulene-2-carbaldehyde (15; Table I)

To a solution of compound 5 (1.8 mmole) in dry tetrahydrofuran (10.0 ml), 1.6 M solution of n-butyl lithium in hexane (5.4 mmole) was added under stirring at −78° C. The reaction mixture was stirred for 15 minutes at −78° C. and then dry N,N-dimethylformamide (4.5 mmole) was added and the reaction mixture was stirred for another 1 hour at room temperature, then it was diluted with water and extracted with ethyl acetate. The organic extract was washed with an aqueous solution of sodium chloride, dried over anhydrous $Na_2SO_4$ and evaporated under reduced pressure. After purification of the evaporation residue by chromatography on a silica gel column, an oily product was isolated.

According to the above process, starting from compounds 6–14 there were prepared the compounds:

1-methyl-1H-8-thia-1,3-diaza-dibenzo[e,h]azulene-2-carbaldehyde;

1-phenethyl-1H-8-oxa-1,3-diaza-dibenzo[e,h]azulene-2-carbaldehyde;

1-phenethyl-1H-8-thia-1,3-diaza-dibenzo[e,h]azulene-2-carbaldehyde;

1-(2-trimethylsilyl-ethoxymethyl)-1H-8-oxa-1,3-diaza-dibenzo[e,h]azulene-2-carbaldehyde;

1-(2-trimethylsilyl-ethoxymethyl)-1H-8-thia-1,3-diaza-dibenzo[e,h]azulene-2-carbaldehyde;

5-chloro-1-(2-trimethylsilyl-ethoxymethyl)-1H-8-oxa-1,3-diaza-dibenzo[e,h]azulene-2-carbaldehyde;

11-chloro-1-(2-trimethylsilyl-ethoxymethyl)-1H-8-oxa-1,3-diaza-dibenzo[e,h]azulene-2-carbaldehyde;

5-chloro-1-(2-trimethylsilyl-ethoxymethyl)-1H-8-thia-1,3-diaza-dibenzo[e,h]azulene-2-carbaldehyde;

11-chloro-1-(2-trimethylsilyl-ethoxymethyl)-1H-8-thia-1,3-diaza-dibenzo[e,h]azulene-2-carbaldehyde (Table I, compounds 16–24).

Example 2

3-(1-Phenethyl-1H-8-thia-1,3-diaza-dibenzo[e,h] azulene-2-yl)-acrylic acid methyl ester (25; Table I)

To a solution of compound 18 (0.82 mmole) in toluene (25.0 ml), methyl(triphenylphosphoranilidene)-acetate (0.82 mmole) was added under stirring. The reaction mixture was heated under stirring and reflux for 3 hours, then it was cooled to room temperature, diluted with water and extracted with dichloromethane. The organic extract was washed with an aqueous sodium chloride solution, dried over anhydrous $Na_2SO_4$ and evaporated under reduced pressure. After purification of the evaporated residue by chromatography on a silica gel column, a crystal product was isolated.

TABLE I

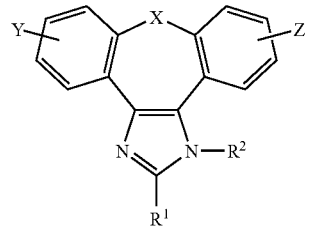

| Comp. | X | Y | Z | $R^1$ | $R^2$ | Ms (m/z) | $^1$H NMR (ppm, $CDCl_3$) |
|---|---|---|---|---|---|---|---|
| 15 | O | H | H | CHO | Me | $MH^+$ 277.4 | 9.97 (s, 1H), 7.94–7.29 (m, 8H), 4.22 (s, 3H) |
| 16 | S | H | H | CHO | Me | $MH^+$ 293.1 | 10.00 (s, 1H), 7.95–7.33 (m, 8H), 4.14 (s, 3H) |
| 17 | O | H | H | CHO | $(CH_2)_2Ph$ | $MH^+$ 367.5 | 9.94 (s, 1H), 7.92–7.16 (m, 13H), 4.89 (t, 2H), 3.14 (t, 2H) |

TABLE I-continued

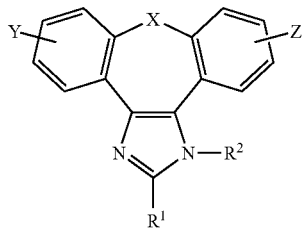

| Comp. | X | Y | Z | R¹ | R² | Ms (m/z) | ¹H NMR (ppm, CDCl₃) |
|---|---|---|---|---|---|---|---|
| 18 | S | H | H | CHO | (CH₂)₂Ph | MH⁺ 383.1 | 9.92 (s, 1H), 7.93–7.04 (m, 13H), 5.13–4.66 (m, 2H), 3.07–2.89 (m, 2H). |
| 19 | O | H | H | CHO | SEMᵃ | MNa⁺ 415.2 | 10.07 (s, 1H), 8.07–7.29 (m, 8H), 5.89 (s, 2H), 3.88 (t, 2H), 1.03 (t, 2H), 0.03 (s, 9H) |
| 20 | S | H | H | CHO | SEM | MNa⁺ 431.1 | 10.03 (s, 1H), 7.95–7.34 (m, 8H), 6.11–5.41 (m, 2H), 3.86–3.66 (m, 2H), 1.00–0.89 (m, 2H), 0.03 (s, 9H) |
| 21 | O | 5-Cl | H | CHO | SEM | MNa⁺+ MeOH 481.1 | 9.99 (s, 1H), 8.08–7.23 (m, 7H), 5.88 (s, 2H), 3.87 (t, 2H), 1.03 (t, 2H), 0.03 (s, 9H) |
| 22 | O | H | 11-Cl | CHO | SEM | MNa⁺+ MeOH 481.1 | 10.01 (s, 1H), 8.10–7.28 (m, 7H), 5.86 (s, 2H), 3.87 (t, 2H), 1.07 (t, 2H), 0.03 (s, 9H) |
| 23 | S | 5-Cl | H | CHO | SEM | MNa⁺ 465.1 | 10.02 (s, 1H), 7.92–7.31 (m, 7H), 6.09 (d, 1H), 5.49 (d, 1H), 3.87–3.67 (m, 2H), 1.01–0.95 (m, 2H), 0.03 (s, 9H) |
| 24 | S | H | 11-Cl | CHO | SEM | MNa⁺ 465.1 | 10.02 (s, 1H), 7.98–7.36 (m, 7H), 6.16 (d, 1H), 5.36 (d, 1H), 3.89–3.71 (m, 2H), 1.08–1.02 (m, 2H), 0.03 (s, 9H) |
| 25 | S | H | H | MAAᵇ | (CH₂)₂Ph | MH⁺ 439.3 | 7.91–6.89 (m, 15H), 4.74–4.35 (m, 2H), 3.82 (s, 3H), 2.89–2.79 (m, 2H) |

ᵃSEM = (CH₃)₃SiCH₂CH₂OCH₂
ᵇMAA = CH₃OCOCH=CH

Example 3

(1-Methyl-1H-8-oxa-1,3-diaza-dibenzo[e,h]azulene-2-yl)-methanol (26; Table II)

To a solution of aldehyde 15 (0.6 mmole) in methanol (20.0 ml), sodium borohydride (0.9 mmole) was added under stirring at 0° C. The reaction mixture was stirred for one hour at 0° C., then it was heated to room temperature and neutralized with acetic acid. Methanol was evaporated under reduced pressure. After evaporation water was added to the residue and then it was extracted with dichloromethane. The organic extract was washed with an aqueous sodium chloride solution, dried over anhydrous Na₂SO₄ and evaporated under reduced pressure. After purification of the evaporation residue by chromatography on a silica gel column, a crystal product was isolated.

According to the above process, starting from compounds 6–14 there were prepared the compounds:

(1-methyl-1H-8-thia-1,3-diaza-dibenzo[e,h]azulene-2-yl)-methanol;
(1-phenethyl-1H-8-oxa-1,3-diaza-dibenzo[e,h]azulene-2-yl)-methanol;
(1-phenethyl-1H-8-thia-1,3-diaza-dibenzo[e,h]azulene-2-yl)-methanol;
[1-(2-trimethylsilyl-ethoxymethyl)-1H-8-oxa-1,3-diaza-dibenzo[e,h]azulene-2-yl]-methanol;
[1-(2-trimethylsilyl-ethoxymethyl)-1H-8-thia-1,3-diaza-dibenzo[e,h]azulene-2-yl]-methanol;
[5-chloro-1-(2-trimethylsilyl-ethoxymethyl)-1H-8-oxa-1,3-diaza-dibenzo[e,h]azulene-2-yl]-methanol;
[11-chloro-1-(2-trimethylsilyl-ethoxymethyl)-1H-8-oxa-1,3-diaza-dibenzo[e,h]azulene-2-yl]-methanol;
[5-chloro-1-(2-trimethylsilyl-ethoxymethyl)-1H-8-thia-1,3-diaza-dibenzo[e,h]azulene-2-yl]-methanol;
[11-chloro-1-(2-trimethylsilyl-ethoxymethyl)-1H-8-thia-1,3-diaza-dibenzo[e,h]azulene-2-yl]-methanol (Table II, compounds 27–35).

Example 4

3-(1-Phenethyl-1H-8-thia-1,3-diaza-dibenzo[e,h]azulene-2-yl)-propan-1-ol (36; Table II)

To a suspension of lithium-aluminum-hydride (2.9 mmole) in dry diethyl-ether (20.0 ml), a solution of ester 25 (0.65 mmole) in dry diethyl-ether (5.0 ml) was added drop by drop. The reaction mixture was stirred for 2 hours at room temperature and then the excess of lithium-aluminum-hydride was destructed by the addition of diethyl-ether and water. The obtained white precipitate was filtered off and, subsequently to drying over anhydrous Na₂SO₄, the filtrate was evaporated under reduced pressure. After purification of the evaporation residue by chromatography on a silica gel column, an oily product was isolated.

TABLE II

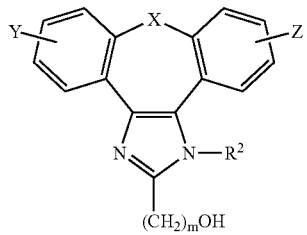

| Comp. | X | Y | Z | m | R² | MS (m/z) | ¹H NMR (ppm) |
|---|---|---|---|---|---|---|---|
| 26 | O | H | H | 1 | Me | MH⁺ 279.1 | 7.76–7.25 (m, 8H), 5.57 (s, 1H), 4.70 (s, 2H), 3.92 (s, 3H) (DMSO-$d_6$) |
| 27 | S | H | H | 1 | Me | MH⁺ 295.2 | 7.78–7.32 (m, 8H), 5.53 (t, 1H), 4.69 (d, 2H), 3.81 (s, 3H) (DMSO-$d_6$) |
| 28 | O | H | H | 1 | (CH₂)₂Ph | MH⁺ 369.3 | — |
| 29 | S | H | H | 1 | (CH₂)₂Ph | MH⁺ 385.4 | 7.83–6.95 (m, 13H), 4.75–4.43 (m, 4H), 2.87–2.72 (m, 2H) (CDCl₃) |
| 30 | O | H | H | 1 | SEM[a] | MH⁺ 395.0 | 7.86–7.31 (m, 8H), 5.70 (t, 1H), 5.63 (s, 2H), 4.75 (d, 2H), 3.69 (t, 2H), 0.94 (t, 2H), 0.03 (s, 9H) (DMSO-$d_6$) |
| 31 | S | H | H | 1 | SEM | MH⁺ 411.0 | 7.91–7.32 (m, 8H), 5.57–5.45 (m, 2H), 5.07 (s, 2H), 4.31 (br, 1H), 3.71–3.45 (m, 2H), 1.27 (t, 2H), 0.03 (s, 9H) (CDCl₃) |
| 32 | O | 5-Cl | H | 1 | SEM | MNa⁺ 451.3 | 8.06–7.18 (m, 7H), 5.69 (br, 2H), 5.43 (s, 2H), 3.88–3.75 (m, 2H), 1.05 (t, 2H), 0.03 (s, 9H) (CDCl₃) |
| 33 | O | H | 11-Cl | 1 | SEM | MNa⁺ 451.3 | 8.03–7.30 (m, 7H), 5.61 (br, 2H), 5.20 (s, 2H), 3.88–3.75 (m, 2H), 1.05 (t, 2H), 0.03 (s, 9H) (CDCl₃) |
| 34 | S | 5-Cl | H | 1 | SEM | MH⁺ 445.1 | — |
| 35 | S | H | 11-Cl | 1 | SEM | MH⁺ 445.1 | — |
| 36 | S | H | H | 3 | (CH₂)₂Ph | MH⁺ 413.2 | 8.01–6.94 (m, 13H), 4.78–4.70 (m, 1H), 4.29–4.19 (m, 1H), 3.66 (t, 2H), 2.80–2.63 (m, 4H), 1.85 (q, 2H) (CDCl₃) |

[a]SEM = (CH₃)₃SiCH₂CH₂OCH₂

Example 5 a) Dimethyl-[2-(1-methyl-1H-8-oxa-1,3-diaza-dibenzo[e,h]azulene-2-ylmethoxy)-ethyl]-amine (I; X=O, Y=Z=H, m=1, R¹=(CH₃)₂N(CH₂)₂OCH₂, R²=CH₃)

To a solution of 2-dimethylaminoethylchloride-hydrochloride (2.9 mmole) in 50% sodium hydroxyde (2.5 ml), a catalytic amount of benzyltriethylammonium chloride and a solution of alcohol 26 (0.2 mmole) in toluene (10.0 ml) were added. The reaction mixture was heated for 3 hours under vigorous stirring and reflux, then it was cooled to room temperature, diluted with water and extracted with dichloromethane. The organic extract was washed with water, dried over anhydrous Na₂SO₄ and evaporated under reduced pressure. After purification of the evaporation residue by chromatography on a silica gel column, an oily product was isolated.

¹H NMR (ppm, CDCl₃): 7.83–7.23 (m, 8H), 4.81 (s, 2H), 4.06 (t, 2H), 3.96 (s, 3H), 3.17 (t, 2H), 2.77 (s, 6H);
MS (m/z): 350.2 [MH⁺].

b) Dimethyl-[3-(1-methyl-1H-8-oxa-1,3-diaza-dibenzo[e,h]azulene-2-ylmethoxy)-propyl]-amine (I; X=O, Y=Z=H, m=1, R¹=(CH₃)₂N(CH₂)₃OCH₂, R²=CH₃)

By a reaction of alcohol 26 (0.2 mmole) and 3-dimethylaminopropylchloride-hydrochloride (2.8 mmole) an oily product was obtained;

¹H NMR (ppm, CDCl₃): 7.84–7.20 (m, 8H), 4.75 (s, 2H), 3.92 (s, 3H), 3.72 (t, 2H), 2.99 (t, 2H), 2.68 (s, 6H), 2.13 (qn, 2H);
MS (m/z): 364.3 [MH⁺].

Example 6 a) Dimethyl-[2-(1-methyl-1H-8-thia-1,3-diaza-dibenzo[e,h]azulene-2-ylmethoxy)-ethyl]-amine (I; X=S, Y=Z=H, m=1, R¹=(CH₃)₂N(CH₂)₂OCH₂, R²=CH₃)

To a solution of 2-dimethylaminoethylchloride-hydrochloride (4.9 mmole) in 50% sodium hydroxyde (3.8 ml), a catalytic amount of benzyltriethylammonium chloride and a solution of alcohol 27 (0.35 mmole) in toluene (10.0 ml) were added. The reaction mixture was heated for 3 hours under vigorous stirring and reflux, then it was cooled to room temperature, diluted with water and extracted with dichloromethane. The organic extract was washed with water, dried over anhydrous Na₂SO₄ and evaporated under reduced pressure. After purification of the evaporation residue by chromatography on a silica gel column, an oily product was isolated.

¹H NMR (ppm, CDCl₃): 7.89–7.32 (m, 8H), 4.86–4.83 (m, 2H), 4.02–3.96 (m, 2H), 3.90 (s, 3H), 3.01 (t, 2H), 2.64 (s, 6H);

MS (m/z): 366.3 [MH⁺].

b) Dimethyl-[3-(1-methyl-1H-8-thia-1,3-diaza-dibenzo[e,h]azulene-2-ylmethoxy)-propyl]-amine (I; X=S, Y=Z=H, m=1, R¹=(CH₃)₂N(CH₂)₃OCH₂, R²=CH₃)

By a reaction of alcohol 27 (0.35 mmole) and 3-dimethylaminopropylchloride-hydrochloride (4.9 mmole) an oily product was obtained;

¹H NMR (ppm, CDCl₃): 7.89–7.28 (m, 8H), 4.82–4.70 (m, 2H), 3.84 (s, 3H), 3.72–3.67 (m, 2H), 2.68 (t, 2H), 2.45 (s, 6H), 1.98 (qn, 2H);

MS (m/z): 380.3 [MH⁺].

Example 7 a) Dimethyl-[2-(1-phenethyl-1H-8-oxa-1,3-diaza-dibenzo[e,h]azulene-2-ylmethoxy)-ethyl]-amine (I; X=O, Y=Z=H, m=1, R¹=(CH₃)₂N(CH₂)₂OCH₂, R²=C₆H₅CH₂CH₂)

To a solution of 2-dimethylaminoethylchloride-hydrochloride (3.1 mmole) in 50% sodium hydroxyde (2.6 ml), a catalytic amount of benzyltriethylammonium chloride and a solution of alcohol 28 (0.22 mmole) in toluene (10.0 ml) were added. The reaction mixture was heated for 3 hours under vigorous stirring and reflux, then it was cooled to room temperature, diluted with water and extracted with dichloromethane. The organic extract was washed with water, dried over anhydrous Na₂SO₄ and evaporated under reduced pressure. After purification of the evaporation residue by chromatography on a silica gel column, an oily product was isolated;

¹H NMR (ppm, CDCl₃): 7.82–6.99 (m, 13H), 4.61 (t, 2H), 4.43 (s, 2H), 3.99 (t, 2H), 3.23 (t, 2H), 2.97 (t, 2H), 2.84 (s, 6H);

MS(m/z): 440.3 [MH⁺].

b) Dimethyl-[3-(1-phenethyl-1H-8-oxa-1,3-diaza-dibenzo[e,h]azulene-2-ylmethoxy)-propyl]-amine (I; X=O, Y=Z=H, m=1, R¹=(CH₃)₂N(CH₂)₃OCH₂, R²=C₆H₅CH₂CH₂)

By a reaction of alcohol 28 (0.21 mmole) and 3-dimethylaminopropylchloride-hydrochloride (2.9 mmole) an oily product was obtained;

¹H NMR (ppm, CDCl₃): 7.84–7.02 (m, 13H), 4.57 (t, 2H), 4.45 (s, 2H), 3.66 (t, 2H), 3.09 (t, 2H), 2.98 (t, 2H), 2.75 (s, 6H), 2.21–2.16 (m, 2H);

MS(m/z): 454.3 [MH⁺].

Example 8 a) Dimethyl-[2-(1-phenethyl-1H-8-thia-1,3-diaza-dibenzo[e,h]azulene-2-ylmethoxy)-ethyl]-amine (I; X=S, Y=Z=H, m=1, R¹=(CH₃)₂N(CH₂)₂OCH₂, R²=C₆H₅CH₂CH₂)

To a solution of 2-dimethylaminoethylchloride-hydrochloride (4.2 mmole) in 50% sodium hydroxyde (3.3 ml), a catalytic amount of benzyltriethylammonium chloride and a solution of alcohol 29 (0.3 mmole) in toluene (10.0 ml) were added. The reaction mixture was heated for 3 hours under vigorous stirring and reflux, then it was cooled to room temperature, diluted with water and extracted with dichloromethane. The organic extract was washed with water, dried over anhydrous Na₂SO₄ and evaporated under reduced pressure. After purification of the evaporation residue by chromatography on a silica gel column, an oily product was isolated.

¹H NMR (ppm, CDCl₃): 7.86–6.95 (m, 13H), 4.75–4.22 (m, 4H), 3.83–3.68 (m, 2H), 2.92–2.67 (m, 4H), 2.55 (s, 6H);

MS(m/z): 456.3 [MH⁺].

b) Dimethyl-[3-(1-phenethyl-1H-8-thia-1,3-diaza-dibenzo[e,h]azulene-2-ylmethoxy)-propyl]-amine (I; X=S, Y=Z=H, m=1, R¹=(CH₃)₂N(CH₂)₃OCH₂, R²=C₆H₅CH₂CH₂)

By a reaction of alcohol 29 (0.5 mmole) and 3-dimethylaminopropylchloride-hydrochloride (7.2 mmole) an oily product was obtained;

¹H NMR (ppm, CDCl₃): 7.87–6.98 (m, 13H), 4.64–4.18 (m, 4H), 3.60 (s, 2H), 2.77–2.74 (m, 4H), 2.49 (s, 6H), 1.99 (m, 2H);

MS(m/z): 470.2 [MH⁺].

Example 9 a) Dimethyl-{2-[1-(2-trimethylsilyl-ethoxymethyl)-1H-8-oxa-1,3-diaza-dibenzo[e,h]azulene-2-ylmethoxy]-ethyl}-amine (I, X=O, Y=Z=H, m=1, R¹=(CH₃)₂N(CH₂)₂OCH₂, R²=(CH₃)₃Si(CH₂)₂OCH₂)

Dimethyl-[2-(1H-8-oxa-1,3-diaza-dibenzo[e,h]azulene-2-ylmethoxy)-ethyl]-amine (I; X=O, Y=Z=H, m=1, R¹=(CH₃)₂N(CH₂)₂OCH₂, R²=H)

To a solution of 2-dimethylaminoethylchloride-hydrochloride (7.5 mmole) in 50% sodium hydroxyde (5.9 ml), a catalytic amount of benzyltriethylammonium chloride and a solution of alcohol 30 (0.53 mmole) in toluene (8 ml) were added. The reaction mixture was heated for 3 hours under the vigorous stirring and reflux, then it was cooled to room temperature, diluted with water and extracted with dichloromethane. The organic extract was washed with water, dried over anhydrous Na₂SO₄ and evaporated under reduced pressure. After purification of the evaporation residue by chromatography on a silica gel column, dimethyl-{2-[1-(2-trimethylsilyl-ethoxymethyl)-1H-8-oxa-1,3-diaza-dibenzo[e,h]azulene-2-ylmethoxy]-ethyl}-amine in the form of an oily product was isolated;

¹H NMR (ppm, CDCl₃): 7.84–7.23 (m, 8H), 5.52 (s, 2H), 4.86 (s, 2H), 3.83 (m, 2H), 3.70 (t, 2H), 3.01 (m, 2H), 2.65 (s, 6H), 0.99 (t, 2H), 0.03 (s, 9H);

MS(m/z): 466.3 [MH⁺].

To a solution of dimethyl-{2-[1-(2-trimethylsilyl-ethoxymethyl)-1H-8-oxa-1,3-diaza-dibenzo[e,h]azulene-2-ylmethoxy]-ethyl}-amine (0.34 mmole) in methanol (9.0 ml), 0.5 M hydrochloric acid in methanol (3.3 ml) was slowly added. The reaction mixture was heated under reflux for 3 hours, then it was cooled to room temperature, neutralized with saturated aqueous sodium hydrogen carbonate solution, diluted with water and extracted with dichloromethane. The organic extract was washed with an aqueous sodium chloride solution, dried over anhydrous Na₂SO₄ and evaporated under reduced pressure. After purification by chromatography on a silica gel column, dimethyl-[2-(1H-8-oxa-1,3-diaza-dibenzo[e,h]azulene-2-ylmethoxy)-ethyl]-amine in the form of an oily product was isolated;

$^1$H NMR (ppm, CDCl$_3$): 8.15–7.17 (m, 8H), 4.86 (s, 2H), 3.89 (t, 2H), 3.12 (t, 2H), 2.75 (s, 6H);
MS(m/z): 336.0 [MH$^+$].

b) Dimethyl-{3-[1-(2-trimethylsilyl-ethoxymethyl)-1H-8-oxa-1,3-diaza-dibenzo[e,h]azulene-yl-methoxy]-propyl}-amine (I; X=O, Y=Z=H, m=1, R$^1$=(CH$_3$)$_2$N(CH$_2$)$_3$OCH$_2$, R$^2$=(CH$_3$)$_3$Si(CH$_2$)$_2$OCH$_2$)

Dimethyl-[3-(1H-8-oxa-1,3-diaza-dibenzo[e,h]azulene-2-ylmethoxy)-propyl]-amine (I; X=O, Y=Z=H, m=1, R$^1$=(CH$_3$)$_2$N(CH$_2$)$_3$OCH$_2$, R$^2$=H)

By a reaction of alcohol 30 (0.49 mmole) and 3-dimethylaminopropylchloride-hydrochloride (6.9 mmole), dimethyl-{3-[1-(2-trimethylsilyl-ethoxymethyl)-1H-8-oxa-1,3-diaza-dibenzo[e,h]azulene-ylmethoxy]-propyl}-amine in the form of an oily product was obtained;
$^1$H NMR (ppm, CDCl$_3$): 7.84–7.23 (m, 8H), 5.49 (s, 2H), 4.80 (s, 2H), 3.72–3.67 (m, 4H), 2.81 (t, 2H), 2.55 (s, 6H), 2.03 (qn, 2H), 0.99 (t, 2H), 0.03 (s, 9H);
MS(m/z): 480.3 [MH$^+$].

After the removal of the N-protecting group and purification of the product by chromatography on a silica gel column, dimethyl-[3-(1H-8-oxa-1,3-diaza-dibenzo[e,h]azulene-2-ylmethoxy)-propyl]-amine in the form of an oily product was obtained;
$^1$H NMR (ppm, CDCl$_3$): 12.32 (s, 1H), 8.17–7.29 (m, 8H), 5.20 (s, 2H), 3.92 (m, 2H), 3.29 (m, 2H), 2.92 (s, 6H), 2.16 (m, 2H);
MS(m/z): 350.1 [MH$^+$].

c) 3-[1-(2- Trimethylsilyl-ethoxymethyl)-1H-8-oxa-1,3-diaza-dibenzo[e,h]azulene-2-ylmethoxy]-propylamine (I; X=O, Y=Z=H, m=1, R$^1$=H$_2$N(CH$_2$)$_3$OCH$_2$, R$^2$=(CH$_3$)$_3$Si(CH$_2$)$_2$OCH$_2$)

3-(1H-8-Oxa-1,3-diaza-dibenzo[e,h]azulene-2-ylmethoxy)-propylamine (I; X=O, Y=Z=H, m=1, R$^1$=H$_2$N(CH$_2$)$_3$OCH$_2$, R$^2$=H)

By a reaction of alcohol 30 (0.94 mmole) and 3-aminopropylchloride-hydrochloride (10.0 mmole), 3-[1-(2-trimethylsilyl-ethoxymethyl)-1H-8-oxa-1,3-diaza-dibenzo[e,h]azulene-2-ylmethoxy]-propylamine in the form of an oily product was obtained;
MS(m/z): 452.2 [MH$^+$].

After the removal of the N-protecting group and purification of the product by chromatography on a silica gel column, 3-(1H-8-oxa-1,3-diaza-dibenzo[e,h]azulene-2-ylmethoxy)-propylamine in the form of an oily product was obtained;
MS(m/z): 322.1 [MH$^+$].

Example 10 a) Dimethyl-{2-[1-(2-trimethylsilyl-ethoxymethyl)-1H-8-thia-1,3-diaza-dibenzo[e,h]azulene-2-ylmethoxy]-ethyl}-amine (I; X=S, Y=Z=H, m=1, R$^1$=(CH$_3$)$_2$N(CH$_2$)$_2$OCH$_2$, R$^2$=(CH$_3$)$_3$Si(CH$_2$)$_2$OCH$_2$)

Dimethyl-[2-(1H-8-thia-1,3-diaza-dibenzo[e,h]azulene-2-ylmethoxy)-ethyl]-amine (I; X=S, Y=Z=H, m=1, R$^1$=(CH$_3$)$_2$N(CH$_2$)$_2$OCH$_2$, R$^2$=H)

To a solution of 2-dimethylaminoethylchloride-hydrochloride (7.6 mmole) in 50% sodium hydroxyde (6.0 ml), a catalytic amount of benzyltriethylammonium chloride and a solution of alcohol 31 (0.55 mmole) in toluene (8.0 ml) were added. The reaction mixture was heated under vigorous stirring and reflux for 3 hours, then it was cooled to room temperature, diluted with water and extracted with dichloromethane. The organic extract was washed with an aqueous sodium chloride solution, dried over anhydrous Na$_2$SO$_4$ and evaporated under reduced pressure. After purification of the evaporation residue by chromatography on a silica gel column, dimethyl-{2-[1-(2-trimethylsilyl-ethoxymethyl)-1H-8-thia-1,3-diaza-dibenzo[e,h]azulene-2-ylmethoxy]-ethyl}-amine in the form of an oily product was isolated;
$^1$H NMR (ppm, CDCl$_3$): 8.15–7.31 (m, 8H), 5.98–5.84 (m, 2H), 5.57–5.35 (m, 2H), 4.41–4.32 (m, 2H), 3.49–3.41 (m, 4H), 2.97 (s, 6H), 0.88 (t, 2H), 0.03 (s, 9H);
MS(m/z): 482.2 [MH$^+$].

To a solution of dimethyl-{2-[1-(2-trimethylsilyl-ethoxymethyl)-1H-8-thia-1,3-diaza-dibenzo[e,h]azulene-2-ylmethoxy]-ethyl}-amine (0.32 mmole) in methanol (7.0 ml), 0.5 M hydrochloric acid in methanol (3.2 ml) was slowly added. The reaction mixture was heated under reflux for 3 hours, then it was cooled to room temperature, neutralized with a saturated aqueous solution of sodium hydrogencarbonate, diluted with water and extracted with dichloromethane. The organic extract was washed with an aqueous sodium chloride solution, dried over anhydrous Na$_2$SO$_4$ and evaporated under reduced pressure. After purification by chromatography on a silica gel column, dimethyl-[2-(1H-8-thia-1,3-diaza-dibenzo[e,h]azulene-2-ylmethoxy)-ethyl]-amine in the form of an oily product was isolated;
$^1$H NMR (ppm, CDCl$_3$): 8.01–7.37 (m, 8H), 5.34–5.30 (m, 2H), 4.11 (m, 2H), 3.42 (m, 2H), 2.94 (m, 6H);
MS(m/z): 352.3 [MH$^+$].

b) Dimethyl-{3-[1-(2-trimethylsilyl-ethoxymethyl)-1H-8-thia-1,3-diaza-dibenzo[e,h]azulene-2-ylmethoxy]-propyl}-amine (I; X=S, Y=Z=H, m=1, R$^1$=(CH$_3$)$_2$N(CH$_2$)$_3$OCH$_2$, R$^2$=(CH$_3$)$_3$Si(CH$_2$)$_2$OCH$_2$)

Dimethyl-[3-(1H-8-thia-1,3-diaza-dibenzo[e,h]azulene-2-ylmethoxy)-propyl]-amine (I; X=S, Y=Z=H, m=1, R$^1$=(CH$_3$)$_2$N(CH$_2$)$_3$OCH$_2$, R$^2$=H)

By a reaction of alcohol 31 (0.58 mmole) and 3-dimethylaminopropylchloride-hydrochloride (8.1 mmole), dimethyl-{3-[1-(2-trimethylsilyl-ethoxymethyl)-1H-8-thia-1,3-diaza-dibenzo[e,h]azulene-2-ylmethoxy]-propyl}-amine in the form of an oily product was obtained;
$^1$H NMR (ppm, CDCl$_3$): 7.95–7.29 (m, 8H), 5.60–5.49 (m, 2H), 4.98–4.87 (m, 2H), 3.83–3.82 (m, 2H), 3.68–3.39 (m, 2H), 3.21–3.18 (m, 2H), 2.82 (s, 6H), 2.26 (m, 2H), 0.91 (t, 2H), 0.03 (s, 9H);
MS(m/z): 496.4 [MH$^+$].

After the removal of the N-protecting group and purification of the product by chromatography on a silica gel column, dimethyl-[3-(1H-8-thia-1,3-diaza-dibenzo[e,h]azulene-2-ylmethoxy)-propyl]-amine in the form of an oily product was obtained;
$^1$H NMR (ppm, CDCl$_3$): 12.00 (bs, 1H), 7.97–7.39 (m, 8H), 5.10 (m, 2H), 3.86 (m, 2H), 3.22 (m, 2H), 2.88 (m, 6H), 2.13 (m, 2H);
MS(m/z): 366.1 [MH$^+$].

Example 11 a) {3-[5-Chloro-1-(2-trimethylsilyl-ethoxymethyl)-1H-8-oxa-1,3-diaza-dibenzo[e,h]azulene-2-yl-methoxy]-propyl}-dimethyl-amine (I; X=O, Y=5-Cl, Z=H, m=1, $R^1$=(CH$_3$)$_2$N(CH$_2$)$_3$OCH$_2$, $R^2$=(CH$_3$)$_3$Si(CH$_2$)$_2$OCH$_2$)

[3-(5-Chloro-1H-8-oxa-1,3-diaza-dibenzo[e,h]azulene-2-ylmethoxy)-propyl]-dimethyl-amine (I; X=O, Y=5-Cl, Z=H, m=1, $R^1$=(CH$_3$)$_2$N(CH$_2$)$_3$OCH$_2$, $R^2$=H)

To a solution of 3-dimethylaininopropylchloride-hydrochloride (2.1 mmole) in 50% sodium hydroxyde (1.7 ml), a catalytic amount of benzyltriethylammonium chloride and a solution of alcohol 32 (0.15 mmole) in toluene (5.0 ml) were added. The reaction mixture was heated under vigorous stirring and reflux for 3 hours, then it was cooled to room temperature, diluted with water and extracted with dichloromethane. The organic extract was washed with an aqueous sodium chloride solution, dried over anhydrous Na$_2$SO$_4$ and evaporated under reduced pressure. After purification of the evaporation residue by chromatography on a silica gel column, {3-[5-chloro-1-(2-trimethylsilyl-ethoxymethyl)-1H-8-oxa-1,3-diaza-dibenzo[e,h]azulene-2-ylmethoxy]-propyl}-dimethyl-amine in the form of an oily product was isolated;

MS(m/z): 514.0 [MH$^+$].

After the removal of the N-protecting group and purification of the product by chromatography on a silica gel column, [3-(5-chloro-1H-8-oxa-1,3-diaza-dibenzo[e,h]azulene-2-ylmethoxy)-propyl]-dimethyl-amine in the form of an oily product was obtained;

$^1$H NMR (ppm, CDCl$_3$): 8.17–7.16 (m, 7H), 4.76 (s, 2H), 3.76 (t, 2H), 3.08 (t, 2H), 2.76 (s, 6H), 2.06 (qn, 2H); MS(m/z): 384.1 [MH$^+$].

b) 3-[5-Chloro-1-(2-trimethylsilyl-ethoxymethyl)-1H-8-oxa-1,3-diaza-dibenzo[e,h]azulene-2-yl-methoxy]-propylamine (I; X=O, Y=5-Cl, Z=H, m=1, $R^1$=H$_2$N(CH$_2$)$_3$OCH$_2$, $R^2$=(CH$_3$)$_3$Si(CH$_2$)$_2$OCH$_2$)

3-(5-Chloro-1H-8-oxa-1,3-diaza-dibenzo[e,h]azulene-2-ylmethoxy)-propylamine (I; X=O, Y=5-Cl, Z=H, m=1, $R^1$=H$_2$N(CH$_2$)$_3$OCH$_2$, $R^2$=H)

By a reaction of alcohol 32 (0.46 mmole) and 3-aminopropylchloride-hydrochloride (6.4 mmole), 3-[5-chloro-1-(2-trimethylsilyl-ethoxymethyl)-1H-8-oxa-1,3-diaza-dibenzo[e,h]azulene-2-ylmethoxy]-propylamine in the form of an oily product was obtained;

MS(m/z): 486.1 [MH$^+$].

After the removal of the N-protecting group and purification of the product by chromatography on a silica gel column, 3-(5-chloro-1H-8-oxa-1,3-diaza-dibenzo[e,h]azulene-2-ylmethoxy)-propylamine in the form of an oily product was obtained;

MS(m/z): 356.2 [MH$^+$].

Example 12 a) {2-[11-Chloro-1-(2-trimethylsilyl-ethoxymethyl)-1H-8-oxa-1,3-diaza-dibenzo[e,h]azulene-2-yl-methoxy]-ethyl}-dimethyl-amine (I; X=O, Y=H, Z=11-Cl, m=1, $R^1$=(CH$_3$)$_2$N(CH$_2$)$_2$OCH$_2$, $R^2$=(CH$_3$)$_3$Si(CH2)$_2$OCH$_2$)

[2-(11-Chloro-1H-8-oxa-1,3-diaza-dibenzo[e,h]azulene-2-ylmethoxy)-ethyl]-dimethyl-amine (I; X=O, Y=H, Z=11-Cl, m=1, $R^1$=(CH$_3$)$_2$N(CH$_2$)$_2$OCH$_2$, $R^2$=H)

To a solution of 2-dimethylaminoethylchloride-hydrochloride (3.6 mmole) in 50% sodium hydroxyde (2.9 ml), a catalytic amount of benzyltriethylammonium chloride and a solution of alcohol 33 (0.26 mmole) in toluene (6 ml) were added. The reaction mixture was heated under vigorous stirring and reflux for 3 hours, then it was cooled to room temperature, diluted with water and extracted with dichloromethane. The organic extract was washed with water, dried over anhydrous Na$_2$SO$_4$ and evaporated under reduced pressure. After purification of evaporation residue by chromatography on a silica gel column, {2-[11-chloro-1-(2-trimethylsilyl-ethoxymethyl)-1H-8-oxa-1,3-diaza-dibenzo[e,h]azulene-2-ylmethoxy]-ethyl}-dimethyl-amine in the form of an oily product was isolated;

MS(m/z): 499.9 [MH$^+$].

To a solution of {2-[11-chloro-1-(2-trimethylsilyl-ethoxymethyl)-1H-8-oxa-1,3-diaza-dibenzo[e,h]azulene-2-ylmethoxy]-ethyl}-dimethyl-amine (0.13 mmole) in methanol (3.0 ml), 0.5 M hydrochloric acid in methanol (1.3 ml) was slowly added. The reaction mixture was heated under reflux for 3 hours, then it was cooled to room temperature, neutralized with a saturated aqueous solution of sodium hydrogencarbonate, diluted with water and extracted with dichloromethane. The organic extract was washed with an aqueous sodium chloride solution, dried over anhydrous Na$_2$SO$_4$ and evaporated under reduced pressure. After purification by chromatography on a silica gel column, [2-(11-chloro-1H-8-oxa-1,3-diaza-dibenzo[e,h]azulene-2-ylmethoxy)-ethyl]-dimethyl-amine in the form of an oily product was isolated;

$^1$H NMR (ppm, CDCl$_3$): 8.12–7.15 (m, 7H), 4.86 (s, 2H), 3.88 (t, 2H), 3.06 (t, 2H), 2.70 (s, 6H); MS(m/z): 370.1 [MH$^+$].

b) {3-[11-Chloro-1-(2-trimethylsilyl-ethoxymethyl)-1H-8-oxa-1,3-diaza-dibenzo[e,h]azulene-2-yl-methoxy]-propyl}-dimethyl-amine (I, X=O, Y=H, Z=11-Cl, m=1, $R^1$=(CH$_3$)$_2$N(CH$_2$)$_3$OCH$_2$, $R^2$=(CH$_3$)$_3$Si(CH$_2$)$_2$OCH$_2$)

[3-(11-Chloro-1H-8-oxa-1,3-diaza-dibenzo[e,h]azulene-2-ylmethoxy)-propyl]-dimethyl-amine (I; X=O, Y=H, Z=11-Cl, m=1, $R^1$=(CH$_3$)$_2$N(CH$_2$)$_3$OCH$_2$, $R^2$=H)

By a reaction of alcohol 33 (0.15 mmole) and 3-dimethylaminopropylchloride-hydrochloride (2.1 mmole), {3-[11-chloro-1-(2-trimethylsilyl-ethoxymethyl)-1H-8-oxa-1,3-diaza-dibenzo[e,h]azulene-2-ylmethoxy]-propyl}-dimethyl-amine in the form of an oily product was obtained;

MS(m/z): 514.2 [MH$^+$].

After the removal of the N-protecting group and purification of the product by chromatography on a silica gel column, [3-(11-chloro-1H-8-oxa-1,3-diaza-dibenzo[e,h]azulene-2-ylmethoxy)-propyl]-dimethyl-amine in the form of an oily product was obtained;

MS(m/z): 384.1 [MH$^+$].

Example 13 a) {2-[5-Chloro-1-(2-trimethylsilyl-ethoxymethyl)-1H-8-thia-1,3-diaza-dibenzo[e,h]azulene-2-yl-methoxy]-ethyl}-dimethyl-amine (I; X=S, Y=5-Cl, Z=H, m=1, $R^1$=(CH$_3$)$_2$N(CH$_2$)$_2$OCH$_2$, $R^2$=(CH$_3$)$_3$Si(CH$_2$)$_2$OCH$_2$)

[2-(5-Chloro-1H-8-thia-1,3-diaza-dibenzo[e,h]azulene-2-ylmethoxy)-ethyl]-dimethyl-amine (I; X=S, Y=5-Cl, Z=H, m=1, $R^1$=(CH$_3$)$_2$N(CH$_2$)$_2$OCH$_2$, $R^2$=H)

To a solution of 2-dimethylaminoethylchloride-hydrochloride (4.8 mmole) in 50% sodium hydroxyde (3.8 ml), a catalytic amount of benzyltriethylammonium chloride and a solution of alcohol 34 (0.35 mmole) in toluene (10.0 ml) were added. The reaction mixture was heated under vigorous stirring and reflux for 3 hours, then it was cooled to room temperature, diluted with water and extracted with dichloromethane. The organic extract was washed with water, dried over anhydrous Na$_2$SO$_4$ and evaporated under reduced pressure. After purification of evaporation residue by chromatography on a silica gel column, {2-[5-chloro-1-(2-trimethylsilyl-ethoxymethyl)-1H-8-thia-1,3-diaza-dibenzo[e,h]azulene-2-ylmethoxy]-ethyl}-dimethyl-amine in the form of an oily product was isolated;

MS(m/z): 516.5 [MH$^+$].

To a solution of {2-[5-chloro-1-(2-trimethylsilyl-ethoxymethyl)-1H-8-thia-1,3-diaza-dibenzo[e,h]azulene-2-ylmethoxy]-ethyl}-dimethyl-amine (0.21 mmole) in methanol (6.0 ml), 0.5 M hydrochloric acid in methanol (2.0 ml) was slowly added. The reaction mixture was heated under reflux for 3 hours, then it was cooled to room temperature, neutralized with a saturated aqueous solution of sodium hydrogencarbonate, diluted with water and extracted with dichloromethane. The organic extract was washed with an aqueous sodium chloride solution, dried over anhydrous Na$_2$SO$_4$ and evaporated under reduced pressure. After purification by chromatography on a silica gel column, [2-(5-chloro-1H-8-thia-1,3-diaza-dibenzo[e,h]azulene-2-ylmethoxy)-ethyl]-dimethyl-amine in the form of an oily product was obtained;

MS(m/z): 386.1 [MH$^+$].

b) {3-[5-Chloro-1-(2-trimethylsilyl-ethoxymethyl)-1H-8-thia-1,3-diaza-dibenzo[e,h]azulene-2-yl-methoxy]-propyl}-dimethyl-amine (I; X=S, Y=5-Cl, Z=H, m=1, $R^1$=(CH$_3$)$_2$N(CH$_2$)$_3$OCH$_2$, $R^2$=(CH$_3$)$_3$Si(CH$_2$)$_2$OCH$_2$)

[3-(5- Chloro-1H-8-thia-1,3-diaza-dibenzo[e,h]azulene-2-ylmethoxy)-propyl]-dimethyl-amine (I; X=S, Y=5-Cl, Z=H, m=1, $R^1$=(CH$_3$)$_2$N(CH$_2$)$_3$OCH$_2$, $R^2$=H)

By a reaction of alcohol 34 (0.34 mmole) and 3-dimethylaminopropylchloride-hydrochloride (4.8 mmole), {3-[5-chloro-1-(2-trimethylsilyl-ethoxymethyl)-1H-8-thia-1,3-diaza-dibenzo[e,h]azulene-2-ylmethoxy]-propyl}-dimethyl-amine in the form of an oily product was obtained;

MS(m/z): 530.2 [MH$^+$].

After the removal of the N-protecting group and purification of the product by chromatography on a silica gel column, [3-(5-chloro-1H-8-thia-1,3-diaza-dibenzo[e,h]azulene-2-ylmethoxy)-propyl]-dimethyl-amine in the form of an oily product was obtained;

MS(m/z): 400.0 [MH$^+$].

Example 14

Dimethyl-{3-[3-(1-phenethyl-1H-8-thia-1,3-diaza-dibenzo[e,h]azulene-2-yl)-propoxy]-propyl}-amine (I; X=S, Y=Z=H, m=3, $R^1$=(CH$_3$)$_2$N(CH$_2$)$_3$O(CH$_2$)$_2$CH$_2$, $R^2$=C$_6$H$_5$CH$_2$CH$_2$)

To a solution of 2-dimethylaminopropylchloride-hydrochloride (2.6 mmole) in 50% sodium hydroxyde (2.2 ml), a catalytic amount of benzyltriethylammonium chloride and a solution of alcohol 36 (0.19 mmole) in toluene (5.0 ml) were added. The reaction mixture was heated under vigorous stirring and reflux for 5 hours. Then it was cooled to room temperature, diluted with water and extracted with dichloromethane. The organic extract was washed with water, dried over anhydrous Na$_2$SO$_4$ and evaporated under reduced pressure. After purification of the evaporation residue by chromatography on a silica gel column, an oily product was isolated;

MS(m/z): 498.4 [MH$^+$].

PREPARATION OF THE STARTING COMPOUNDS

Process A 1H-8-Oxa-1,3-diaza-dibenzo[e,h]azulene (1; Table III)

To a solution of dibenzo[b,f]oxepine-10,11-dione (9.6 mmole) in acetic acid (30.0 ml), ammonium acetate (96.0 mmole) and paraformaldehyde (11.5 mmole) were added. The reaction mixture was heated under stirring and reflux for 4 hours, then it was cooled to room temperature, diluted with water, neutralized with ammonium hydroxide and extracted with ethyl acetate. The organic extract was washed with an aqueous sodium chloride solution, dried over anhydrous Na$_2$SO$_4$ and evaporated under reduced pressure. After purification of the evaporation residue by chromatography on a silica gel column, a crystal product was isolated.

According to the above process starting from the compounds
dibenzo[b,f]thiepine-10,11-dione,
2-chloro-dibenzo[b,f]oxepine-10,11-dione,
2-chloro-dibenzo[b,f]thiepine-10,11-dione, there were prepared
1H-8-thia-1,3-diaza-dibenzo[e,h]azulene,
5-chloro-1H-8-oxa-1,3-diaza-dibenzo[e,h]azulene,
5-chloro-1H-8-thia-1,3-diaza-dibenzo[e,h]azulene (Table III, compounds 2–4).

Process B

1-Methyl-1H-8-oxa-1,3-diaza-dibenzo[e,h]azulene (5; Table III)

To a solution of compound 1 (2.8 mmole) in dry tetrahydrofuran (20.0 ml), a 60% suspension of sodium hydride in mineral oil (8.4 mmole) was added under stirring at 0° C. The reaction mixture was stirred for 30 minutes at 0° C., then methyl iodide (4.2 mmole) was added thereto and the reaction mixture was heated under stirring and reflux for another 5 hours. Then it was cooled to room temperature, diluted with water and extracted with dichloromethane. The organic extract was washed with an aqueous sodium chloride solution, dried over anhydrous Na₂SO₄ and evaporated under reduced pressure. After purification of the evaporated residue by chromatography on a silica gel column, a crystal product was isolated.

According to the above process starting from the compound 2, 1-methyl-1H-8-thia-1,3-diaza-dibenzo[e,h]azulene (6; Table III) was prepared.

Process C

1-Phenethyl-1H-8-oxa-1,3-diaza-dibenzo[e,h]azulene (7; Table III)

To a solution of compound 1 (2.6 mmole) in dry tetrahydrofuran (20.0 ml), a 60% suspension of sodium hydride in mineral oil (8.0 mmole) was added under stirring at 0° C. The reaction mixture was stirred for 30 minutes at 0° C., then 2-phenylethyl-bromide (5.2 mmole) and a catalytic amount of tetra-n-butylammonium iodide were added thereto and the reaction mixture was heated under stirring and reflux for 5 hours. Then it was cooled to room temperature, diluted with water and extracted with dichloromethane. The organic extract was washed with an aqueous sodium chloride solution, dried over anhydrous Na₂SO₄ and evaporated under reduced pressure. After purification of the evaporation residue by chromatography on a silica gel column, a crystal product was isolated.

According to the above process starting from the compound 2, 1-phenethyl-1H-8-thia-1,3-diaza-dibenzo[e,h]azulene (8; Table III) was prepared.

Process D 1-(2-Trimethylsilyl-ethoxymethyl)-1H-8-oxa-1,3-diaza-dibenzo[e,h]azulene (9; Table III)

To a solution of compound 1 (1.1 mmole) in dry tetrahydrofuran (7.0 ml), a 60% suspension of sodium hydride in mineral oil (3.2 mmole) was added under stirring at 0° C. The reaction mixture was stirred for 30 minutes at 0° C., then 2-(trimethylsilyl)ethoxymethyl-chloride (1.1 mmole) was added thereto and the reaction mixture was stirred for another 3 hours at room temperature. Then it was diluted with water and extracted with dichloromethane. The organic extract was washed with an aqueous sodium chloride solution, dried over anhydrous Na₂SO₄ and evaporated under reduced pressure. After purification of the evaporation residue by chromatography on a silica gel column, a crystal product was isolated.

According to the above process starting from the compound 2, 1-(2-trimethylsilyl-ethoxymethyl)-1H-8-thia-1,3-diaza-dibenzo[e,h]azulene (10; Table III) was prepared.

Starting from compound 3 there were prepared isomers 5-chloro-1-(2-trimethylsilyl-ethoxymethyl)-1H-8-oxa-1,3-diaza-dibenzo[e,h]azulene,
11-chloro-1-(2-trimethylsilyl-ethoxymethyl)-1H-8-oxa-1,3-diaza-dibenzo[e,h]azulene, and starting from compound 4 there were prepared isomers 5-chloro-1-(2-trimethylsilyl-ethoxymethyl)-1H-8-thia-1,3-diaza-dibenzo[e,h]azulene,
11-chloro-1-(2-trimethylsilyl-ethoxymethyl)-1H-8-thia-1,3-diaza-dibenzo[e,h]azulene (Table III, compounds 1–14).

TABLE III

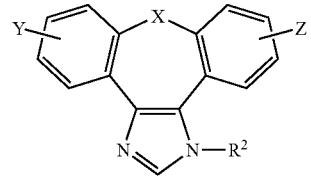

| Comp. | X | Y | Z | R² | MS (m/z) | ¹H NMR (ppm) |
|---|---|---|---|---|---|---|
| 1 | O | H | H | H | MH⁺ 235.4 | 12.92 (s, 1H), 7.96 (s, 1H), 7.65–7.26 (m, 8H) (DMSO-d₆) |
| 2 | S | H | H | H | MH⁺ 250.8 | 12.91 (s, 1H), 7.99 (s, 1H), 7.84–7.35 (m, 8H) (DMSO-d₆) |
| 3 | O | 5-Cl | H | H | MH⁺ 268.8 | 13.03 (s, 1H), 8.00 (s, 1H), 7.75–7.29 (m, 7H) (DMSO-d₆) |
| 4 | S | 5-Cl | H | H | MH⁺ 284.9 | 13.06 (s, 1H), 8.04 (s, 1H), 7.77–7.42 (m, 7H) (DMSO-d₆) |
| 5 | O | H | H | Me | MH⁺ 249.2 | 7.95 (s, 1H), 7.91–7.21 (m, 8H), 3.95 (s, 3H) (CDCl₃) |
| 6 | S | H | H | Me | MH⁺ 265.1 | 7.94–7.28 (m, 9H), 3.88 (s, 3H) (CDCl₃) |
| 7 | O | H | H | (CH₂)₂Ph | MH⁺ 339.3 | 7.96–7.09 (m, 14H), 4.55 (t, 2H), 3.11 (t, 2H) (CDCl₃) |
| 8 | S | H | H | (CH₂)₂Ph | MH⁺ 355.3 | 8.25 (s, 1H), 7.98–7.03 (m, 13H), 4.73–4.44 (m, 2H), 2.98 (t, 2H) (CDCl₃) |
| 9 | O | H | H | SEMᵃ | MH⁺ 365.2 | 8.38 (s, 1H), 7.92–7.20 (m, 8H), 5.50 (s, 2H), 3.77 (t, 2H), 0.99 (t, 2H), 0.03 (s, 9H) (CDCl₃) |
| 10 | S | H | H | SEM | MH⁺ 381.3 | 8.57 (s, 1H), 8.01–7.37 (m, 8H), 5.62–5.38 (m, 2H), 3.92–3.66 (m, 2H), 1.06–0.95 (m, 2H), 0.03 (s, 9H) (CDCl₃) |
| 11 | O | 5-Cl | H | SEM | MH⁺ 399.1 | 8.49 (s, 1H), 8.37–7.21 (m, 7H), 5.55 (s, 2H), 3.82 (t, 2H), 1.04 (t, 2H), 0.03 (s, 9H) (CDCl₃) |

TABLE III-continued

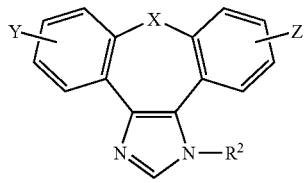

| Comp. | X | Y | Z | R² | MS (m/z) | ¹H NMR (ppm) |
|---|---|---|---|---|---|---|
| 12 | O | H | 11-Cl | SEM | MH⁺ 399.1 | 8.48 (s, 1H), 7.97–7.27 (m, 7H), 5.53 (s, 2H), 3.83 (t, 2H), 1.07 (t, 2H), 0.03 (s, 9H) (CDCl₃) |
| 13 | S | 5-Cl | H | SEM | MH⁺ 415.0 | 8.36 (s, 1H), 8.00–7.33 (m, 7H), 5.59–5.48 (m, 2H), 3.93–3.84 (m, 1H), 3.75–3.66 (m, 1H), 1.08–1.03 (m, 2H), 0.03 (s, 9H) (CDCl₃) |
| 14 | S | H | 11-Cl | SEM | MHH⁺ 414.9 | 8.40 (s, 1H), 8.07–7.33 (m, 7H), 5.67–5.49 (m, 2H), 3.93–3.81 (m, 2H), 1.10 (m, 2H), 0.03 (s, 9H) (CDCl₃) |

ᵃSEM = (CH₃)₃SiCH₂CH₂OCH₂

The invention claimed is:

1. A compound of formula I:

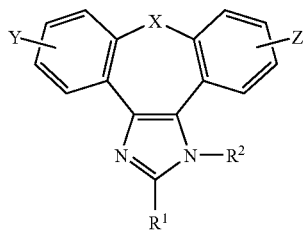

I wherein

X is O, S, S(=O), or S(=O2);

Y and Z are each independently selected from the group consisting of hydrogen, halogen, $C_1$–$C_4$ alkyl, $C_2$–$C_4$ alkenyl, $C_2$–$C_4$ alkynyl, halo-$C_1$–$C_4$ alkyl, hydroxy, $C_1$–$C_4$ alkoxy, trifluoromethoxy, $C_1$–$C_4$ alkanoyl, amino, amino-$C_1$–$C_4$-alkyl, N-($C_1$–$C_4$-alkyl)amino, N,N-di($C_1$–$C_4$-alkyl)amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano, and nitro;

R¹ is selected from the group consisting of halogen, hydroxy, $C_1$–$C_7$-alkoxy, aryloxy, amino, N-($C_1$–$C_7$ alkyl)amino, N,N-di($C_1$–$C_7$-alkyl)amino, ($C_1$–$C_7$-alkyl)amino, amino-$C_1$–$C_7$ alkoxy, $C_1$–$C_7$ alkanoyl, aroyl, $C_1$–$C_7$ alkanoyloxy, carboxy, an optionally substituted $C_1$–$C_7$ alkyloxycarbonyl or aryloxycarbonyl, carbamoyl, N-($C_1$–$C_7$-alkyl)carbamoyl, N,N-di($C_1$–$C_7$-alkyl)carbamoyl, cyano, nitro, and a substituent of the formula II:

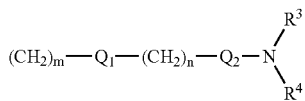

II wherein

R³ and R⁴ are each independently selected from the group consisting of hydrogen, $C_1$–$C_4$ alkyl, aryl or together with the nitrogen atom to which they are attached form an optionally substituted heterocycle or heteroaryl;

m is an integer from 1 to 3;

n is an integer from 0 to 3;

Q₁ and Q₂ are each independently selected from the group consisting of oxygen, sulfur,

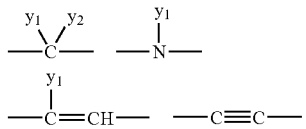

wherein y₁ and y₂ are each independently selected from the group consisting of hydrogen, halogen, an optionally substituted $C_1$–$C_4$ alkyl or aryl, hydroxy, $C_1$–$C_4$ alkoxy, $C_1$–$C_4$ alkanoyl, thiol, $C_1$–$C_4$ alkylthio, sulfonyl, $C_1$–$C_4$ alkylsulfonyl, sulfinyl, $C_1$–$C_4$ alkylsulfinyl, cyano, and nitro or y₁ and y₂ taken together with the carbon atom to which they are attached form a carbonyl or imino group;

R² is selected from the group consisting of hydrogen, optionally substituted $C_1$–$C_7$ alkyl or aryl, and a protecting group selected from the group consisting of formyl, $C_1$–$C_7$ alkanoyl, $C_1$–$C_7$ alkoxycarbonyl, arylalkyloxycarbonyl, aroyl, arylalkyl, and $C_1$–$C_7$ alkylsilyl;

and pharmaceutically acceptable salts and solvates thereof.

2. The compound of claim 1, wherein X is S or O.

3. The compound of claim 2, wherein Y and Z are each independently H or Cl.

4. The compound of claim 3, wherein R¹ is CHO or CH₃OCOCH=CH and R² is H, CH₃, C₆H₅CH₂CH₂ or (CH₃)₃SiCH₂CH₂OCH₂.

5. The compound of claim 3, wherein R¹ is (CH₂)ₘOH and R² is H, CH₃, C₆H₅CH₂CH₂ or (CH₃)₃SiCH₂CH₂OCH₂.

6. The compound of claim 5, wherein m is 1 or 3.

7. The compound of claim 3, wherein R¹ is

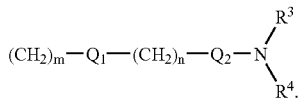

II

8. The compound of claim 7, wherein m is 1 or 3, $Q_1$ is O, n is 1 or 2, $Q_2$ is $CH_2$, $R^2$ is H, $CH_3$, $C_6H_5CH_2CH_2$ or $(CH_3)_3SiCH_2CH_2OCH_2$, and $R^3$ and are each independently H or $CH_3$.

9. The compound of claim 4 selected from the group consisting of:
- 1-methyl-1H-8-oxa-1,3-diaza-dibenzo[e,h]azulene-2-carbaldehyde;
- 1-methyl-1H-8-thia-1,3-diaza-dibenzo[e,h]azulene-2-carbaldehyde;
- 1-phenethyl-1H-8-oxa-1,3-diaza-dibenzo[e,h]azulene-2-carbaldehyde;
- 1-phenethyl-1H-8-thia-1,3-diaza-dibenzo[e,h]azulene-2-carbaldehyde;
- 1-(2-trimethylsilyl-ethoxymethyl)-1H-8-oxa-1,3-diaza-dibenzo[e,h]azulene-2-carbaldehyde;
- 1-(2-trimethylsilyl-ethoxymethyl)-1H-8-thia-1,3-diaza-dibenzo[e,h]azulene-2-carbaldehyde;
- 5-chloro-1-(2-trimethylsilyl-ethoxymethyl)-1H-8-oxa-1,3-diaza-dibenzo[e,h]azulene-2-carbaldehyde;
- 11-chloro-1-(2-trimethylsilyl-ethoxymethyl)-1H-8-oxa-1,3-diaza-dibenzo[e,h]azulene-2-carbaldehyde;
- 5-chloro-1-(2-trimethylsilyl-ethoxymethyl)-1H-8-thia-1,3-diaza-dibenzo[e,h]azulene-2-carbaldehyde;
- 11-chloro-1-(2-trimethylsilyl-ethoxymethyl)-1H-8-thia-1,3-diaza-dibenzo[e,h]azulene-2-carbaldehyde; and
- 3-(1-phenethyl-1H-8-thia-1,3-diaza-dibenzo[e,h]azulene-2-yl)-acrylic acid methyl ester.

10. The compound of claim 6 selected from the group consisting of:
- (1-methyl-1H-8-oxa-1,3-diaza-dibenzo[e,h]azulene-2-yl)-methanol;
- (1-methyl-1H-8-thia-1,3-diaza-dibenzo[e,h]azulene-2-yl)-methanol;
- (1-phenethyl-1H-8-oxa-1,3-diaza-dibenzo[e,h]azulene-2-yl)-methanol;
- (1-phenethyl-1H-8-thia-1,3diaza-dibenzo[e,h]azulene-2-yl)-methanol;
- [1-(2-trimethylsilyl-ethoxymethyl)-1H-8-oxa-1,3-diaza-dibenzo[e,h]azulene-2-yl]-methanol;
- [1-(2-trimethylsilyl-ethoxymethyl)-1H-8-thia-1,3-diaza-dibenzo[e,h]azulene-2-yl]-methanol;
- [5-chloro-1-(2-trimethylsilyl-ethoxymethyl)-1H-8-oxa-1,3-diaza-dibenzo[e,h]azulene-2-yl]-methanol;
- [11-chloro-1-(2-trimethylsilyl-ethoxymethyl)-1H-8-oxa-1,3-diaza-dibenzo[e,h]azulene-2-yl]-methanol;
- [5-chloro-1-(2-trimethylsilyl-ethoxymethyl)-1H-8-thia-1,3-diaza-dibenzo[e,h]azulene -2-yl]-methanol;
- [11-chloro-1-(2-trimethylsilyl-ethoxymethyl)-1H-8-thia-1,3-diaza-dibenzo[e,h]azulene-2-yl]-methanol; and
- 3-(1-phenethyl-1H-8-thia-1,3-diaza-dibenzo[e,h]azulene-2-yl)-propan-1-ol.

11. The compound of claim 8 selected from the group consisting of:
- dimethyl-[2-(1-methyl-1H-8-oxa-1,3-diaza-dibenzo[e,h]azulene-2-ylmethoxy)-ethyl]-amine;
- dimethyl-[3-(1-methyl-1H-8-oxa-1,3-diaza-dibenzo[e,h]azulene-2-ylmethoxy)-propyl]-amine;
- dimethyl-[2-(1-methyl-1H-8-thia-1,3-diaza-dibenzo[e,h]azulene-2-ylmethoxy)-ethyl]-amine;
- dimethyl-[3-(1-methyl-1H-8-thia-1,3-diaza-dibenzo[e,h]azulene-2-ylmethoxy)-propyl]-amine;
- dimethyl-[2-(1-phenethyl-1H-8-oxa-1,3-diaza-dibenzo[e,h]azulene-2-ylmethoxy)-ethyl]-amine;
- dimethyl-[3-(1-phenethyl-1H-8-oxa-1,3-diaza-dibenzo[e,h]azulene-2-ylmethoxy)-propyl]-amine;
- dimethyl-[2-(1-phenethyl-1H-8-thia-1,3-diaza-dibenzo[e,h]azulene-2-ylmethoxy)-ethyl]-amine;
- dimethyl-[3-(1-phenethyl-1H-8-thia-1,3-diaza-dibenzo[e,h]azulene-2-ylmethoxy)-propyl]-amine;
- dimethyl-{2-[1-(2-trimethylsilyl-ethoxymethyl)-1H-8-oxa-1,3-diaza-dibenzo[e,h]azulene-2-ylmethoxy]-ethyl}-amine;
- dimethyl-[2-(1H-8-oxa-1,3-diaza-dibenzo[e,h]azulene-2-ylmethoxy)-ethyl]-amine;
- dimethyl-{3-[1-(2-trimethylsilyl-ethoxymethyl)-1H-8-oxa-1,3-diaza-dibenzo[e,h]azulene-ylmethoxy]-propyl}-amine;
- dimethyl-[3-(1H-8-oxa-1,3-diaza-dibenzo[e,h]azulene-2-ylmethoxy)-propyl]-amine 3-[1-(2-trimethylsilyl-ethoxymethyl)-1H-8-oxa-1,3-diaza-dibenzo[e,h]azulene-2-ylmethoxy-propylamine;
- 3-(1H-8-oxa-1,3-diaza-dibenzo[e,h]azulene-2-ylmethoxy)-propylamine;
- dimethyl-{2-[1-(2-trimethylsilyl-ethoxymethyl)-1H-8-thia-1,3-diaza-dibenzo[e,h]azulene-2-ylmethoxy]-ethyl}-amine;
- dimethyl-[2-(1H-8-thia-1,3-diaza-dibenzo[e,h]azulene-2-ylmethoxy)-ethyl]-amine;
- dimethyl-{3-[1-(2-trimethylsilyl-ethoxymethyl)-1H-8-thia-1,3-diaza-dibenzo[e,h]azulene-2-ylmethoxy-propyl}-amine;
- dimethyl-[3-(1H-8-thia-1,3-diaza-dibenzo[e,h]azulene-2-ylmethoxy)-propyl)-amine {3-[5-chloro-1-(2-trimethylsilyl-ethoxymethyl)-1H-8-oxa-1,3-diaza-dibenzo[e,h]azulene-2-ylmethoxy]-propyl}-dimethyl-amine;
- 3-(5-chloro-1H-8-oxa-1,3-diaza-dibenzo[e,h]azulene-2-ylmethoxy)-propyl]-dimethyl-amine;
- 3-[5-chloro-1-(2-trimethylsilyl-ethoxymethyl)-1H-8-oxa-1,3-diaza-dibenzo[e,h]azulene-2-ylmethoxy]-propylamine;
- 3-(5-chloro-1H-8-oxa-1,3-diaza-dibenzo[e,h]azulene-2-ylmethoxy)-propylamine;
- {2-[11-chloro-1-(2-trimethylsilyl-ethoxymethyl)-1H-8-oxa-1,3-diaza-dibenzo[e,h]azulene-2-ylmethoxy]-ethyl}-dimethyl-amine;
- [2-(11-chloro-1H-8-oxa-1,3-diaza-dibenzo[e,h]azulene-2-ylmethoxy)-ethyl]-dimethyl-amine;
- {3-[11-chloro-1-(2-trimethylsilyl-ethoxymethyl)-1H-8-oxa-1,3-diaza-dibenzo[e,h]azulene-2-ylmethoxy]-propyl}-dimethyl-amine;
- [3-(11-chloro-1H-8-oxa-1,3-diaza-dibenzo[e,h]azulene-2-ylmethoxy)-propyl]-dimethyl-amine;
- {2-[5-chloro-1-(2-trimethylsilyl-ethoxymethyl)-1H-8-thia-1,3-diaza-dibenzo[e,h]azulene-2-ylmethoxy]-ethyl}-dimethyl-amine;
- [2-(5-chloro-1H-8-thia-1,3-diaza-dibenzo[e, h]azulene-2-ylmethoxy)-ethyl]-dimethyl-amine;
- {3-[5-chloro-1-(2-trimethylsilyl-ethoxymethyl)-1H-8-thia-1,3-diaza-dibenzo[e,h]azulene-2-ylmethoxy]-propyl}-dimethyl-amine;
- [3-(5-chloro-1H-8-thia-1,3-diaza-dibenzo[e,h]azulene-2-ylmethoxy)-propyl]-dimethyl-amine;
- dimethyl-{3-[3-(1-phenethyl-1H-8-thia-1,3-diaza-dibenzo[e,h]azulene-2-yl)-propoxy]-propyl}-amine;

and pharmaceutically acceptable salts thereof.

12. Process for the preparation of compounds of the formula

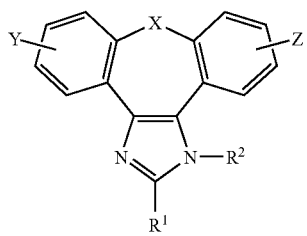

I wherein

X is O, S, S (=O), or S (=O2);

Y and Z are each independently selected from the group consisting of hydrogen halogen, $C_1$–$C_4$ alkyl, $C_2$–$C_4$ alkenyl, $C_2$–$C_4$ alkinyl, halo-$C_1$–$C_4$ alkyl, hydroxy, $C_1$–$C_4$ alkoxy, trifluoromethoxy, $C_1$–$C_4$ alkanoyl, amino, amino-$C_1$–$C_4$-alkyl, N-($C_1$–$C_4$-alkyl) amino, N,N-di($C_1$–$C_4$ alkyl) amino, thiol, $C_1$–$C_4$ alkylthio, sulfonyl, $C_1$–$C_4$ alkylsulfonyl, sulfinyl, $C_1$–$C_4$ alkylsulfinyl, carboxy, $C_1$–$C_4$ alkoxycarbonyl, cyano, nitro;

$R^1$ is selected from the group consisting of halogen, hydroxy, $C_1$–$C_7$ alkoxy, aryloxy, amino, N-($C_1$–$C_7$ alkyl) amino, N, N-di ($C_1$–$C_7$ alkyl) amino, ($C_1$–$C_7$ alkyl) amino, amino-$C_1$–$C_7$ alkoxy, $C_1$–$C_7$-alkanoyl, aroyl, $C_1$–$C_7$-alkanoyloxy, carboxy, an optionally substituted $C_1$–$C_7$-alkyloxycarbonyl or aryloxycarbonyl, carbamoyl, N-($C_1$–$C_7$ alkyl) carbamoyl, N,N-di($C_1$–$C_7$ alkyl) carbamoyl, cyano, nitro, and a substituent of the formula II

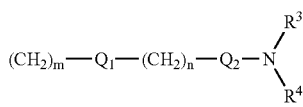

II wherein $R^3$ and $R^4$ are each independently selected from the group consisting of hydrogen, $C_1$–$C_4$-alkyl, aryl or, together with the nitrogen atom to which they are attached, form an optionally substituted heterocycle or heteroaryl;

m is an integer from 1 to 3;

n is an integer from 0 to 3;

$Q_1$ and $Q_2$ are each, independently selected from the group consisting of, oxygen, sulfur or groups:

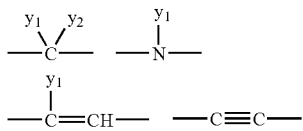

wherein $y_1$, and $y_2$ are each independently selected from the group consisting of hydrogen, halogen, an optionally substituted $C_1$–$C_4$ alkyl or aryl, hydroxy, $C_1$–$C_4$ alkoxy, $C_1$–$C_4$ alkanoyl, thiol, $C_1$–$C_4$ alkylthio, sulfonyl, $C_1$–$C_4$ alkylsulfonyl, sulfinyl, $C_1$–$C_4$ alkylsulfinyl, cyano, and nitro or $y_1$ and $y_2$ taken together with the carbon atom to which they are attached form a carbonyl or imino group;

$R^2$ is selected from the group consisting of hydrogen, optionally substituted $C_1$–$C_7$ alkyl or aryl, and a protecting group selected from the group consisting of: formyl, $C_1$–$C_7$ alkanoyl, $C_1$–$C_7$ alkoxycarbonyl, arylalkyloxycarbonyl, aroyl, arylalkyl and $C_1$–$C_7$ alkylsilyl; and pharmacologically acceptable salts and solvates thereof, . . . the process comprising:

a) for compounds of the formula I, wherein $R^1$ has a meaning of CHO, a formylation of the compounds of the formula III

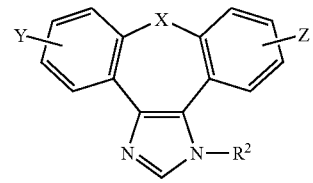

III with N,N-dimethylformamide;

b) for a compound of the formula I, wherein $Q_1$ is —O—, a reaction of an alcohol of the formula IV

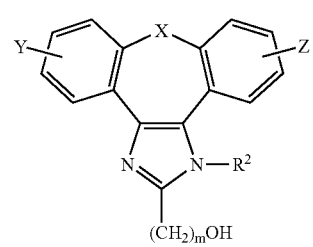

IV with a compound of the formula V

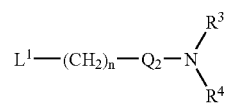

V wherein L1 is a leaving group, c) for a compound of the formula I, wherein $Q_1$ is —O—, —NH—, —S— or —C≡C—, a reaction of a compound of the formula IVa

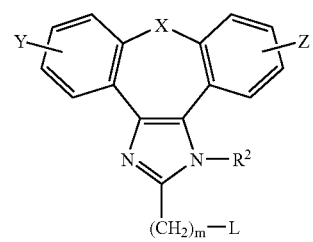

IVa wherein L is a leaving group, with a compound of the formula Va

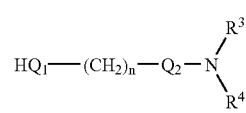

Va d) for a compound of the formula I, wherein $Q_1$ is —O—, —NH— or —S—, a reaction of a compound of the formula IVb:

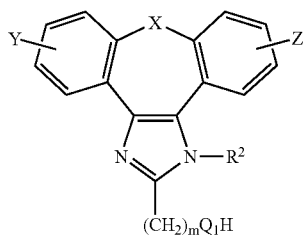

with a compound of the formula V, wherein $L^1$ is a leaving group;

e) for compounds of the formula I, wherein $Q_1$ is —C=C—, a reaction of a compound of the formula IVb, wherein $Q_1$ is carbonyl, with a phosphorous ylide.

13. A method for treating inflammation associated with TNF-α comprising administering to a subject in need of treatment an effective amount of a compound according to claim 7.

* * * * *

UNITED STATES PATENT AND TRADEMARK OFFICE
CERTIFICATE OF CORRECTION

PATENT NO. : 7,166,583 B2
APPLICATION NO. : 10/515711
DATED : January 23, 2007
INVENTOR(S) : Mercep et al.

It is certified that error appears in the above-identified patent and that said Letters Patent is hereby corrected as shown below:

Column 29, Claim 1, line 49 should read:
  -- hydroxy, $C_1$-$C_7$-alkoxy, aryloxy, amino, N-($C_1$-$C_7$, --

Column 30, Claim 1, line 35 should read:

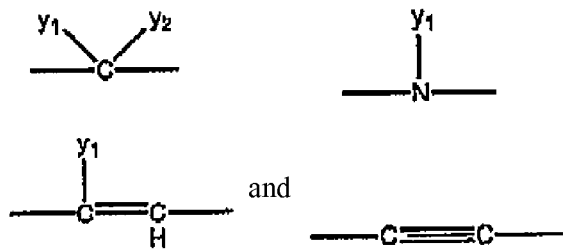

Column 33, Claim 12, line 18 should read:

-- consisting of hydrogen halogen, $C_1$-$C_4$ alkyl, $C_2$-$C_4$ --

Signed and Sealed this

Twenty-third Day of October, 2007

JON W. DUDAS
*Director of the United States Patent and Trademark Office*